(12) United States Patent
Reynolds et al.

(10) Patent No.: US 7,588,752 B2
(45) Date of Patent: Sep. 15, 2009

(54) ANTIMICROBIAL PEPTIDES

(75) Inventors: Eric C. Reynolds, North Balwyn (AU);
Stuart G. Dashper, Hawthorn (AU);
Neil M. O'Brien-Simpson, Brunswick (AU); Gert H. Talbo, Viewbank (AU);
Marina Malkoski, Nunawading (AU)

(73) Assignee: The University of Melbourne, Parkville, Victoria (AU)

( * ) Notice: Subject to any disclaimer, the term of this patent is extended or adjusted under 35 U.S.C. 154(b) by 390 days.

(21) Appl. No.: 10/280,833

(22) Filed: Oct. 24, 2002

(65) Prior Publication Data

US 2003/0195150 A1    Oct. 16, 2003

Related U.S. Application Data

(63) Continuation of application No. 09/554,997, filed as application No. PCT/AU98/00972 on Nov. 24, 1998, now abandoned.

(30) Foreign Application Priority Data

Nov. 24, 1997    (AU) ...................................... PP0514

(51) Int. Cl.
*A61Q 11/00* (2006.01)
*A61K 35/20* (2006.01)
*A23J 3/10* (2006.01)
(52) U.S. Cl. .......................... 424/49; 530/300; 530/360
(58) Field of Classification Search ..................... 514/2, 514/12, 13; 530/300
See application file for complete search history.

(56) References Cited

U.S. PATENT DOCUMENTS 4,994,441 A * 2/1991 Nesser ............................ 514/8
5,583,198 A * 12/1996 Whittaker .................... 530/345
5,846,732 A * 12/1998 Collin et al. .................. 435/7.1

FOREIGN PATENT DOCUMENTS

JP         07278013 A  * 10/1995
WO         WO 9109837   *  7/1991
WO         WO 95/31556 A1  11/1995

OTHER PUBLICATIONS

Well Additivity of Mutational Effects in Proteins. Biochemistry vol. 29/37 pp. 8509-8517(1990).*
Willis et al. Characterisation of cloned cDNAs for bovine (alpha)s1, (beta) and (kappa) caseins and (beta)-lactoglobulin. Manipulation and expression of genes in eukaryotes pp. 25-26 (1983).*
Minkiewicz et al., Reversed-phase high performance liquid chromatographic separation of bovine k-casein macropeptide and characterization of isolated fractions. Journal of Chromatography A, 743:123-135 (1996).*
Ferjancic-Biagini et al. Acylation of food proteins and hydrolysis by digestive enzymes: A review. Journal of Food Biochemistry 22(4), 331-345 (Sep. 1998).*
Molle' et al., Heterogeneity of the bovine k-casein caseinomacropeptide, resolved by liquid chromatography on-line with electrospray ionizaton mass spectrometry. Journal of Chromatography A, vol. 708, pp. 223-230 (1995).*
Database Uniprot Kappa-Casein (fragment) May 1, 1997, Wollard J.R. et al., retrieved from EBI Database accession No. P79094, XP002293161.
Database Uniprot Kappa-casein (fragment)., May 1, 1997, Woollard J.R. et al., retrieved by EBI, Database accession No. P79093, XP002293162.
Addy et al. Effects of a Zinc Citrate Mouthwash on Dental Plaque and Salivary Bacteria. Journal of Clinical Periodontology, 1980, vol. 7, pp. 309-315.
Addy, Rationale for chemotherapy in the treatment of periodontal disease, In: Periodontology Today (Guggenheim B (ed)), 1988, pp. 281-289, Karger, Basel.
Bevins et al. Peptides from frog skin. Annual Review of Biochemistry, 1990, vol. 59, pp. 395-414.
Boman et al. Cell-free immunity in insects. 1987, Annual Review of Microbiology, vol. 41, pp. 103-126.
Brown et al. Periodontal diseases in the US in 1981: Prevalence, severity, extent and role in tooth mortality. Journal of Periodontology, 1989, vol. 60, pp. 363-370.
Casteels et al. Apidaecins: antibacterial peptides from honeybees. The EMBO Journal, 1989, vol. 8, pp. 2387-2391.
Christersson et al. Specific subgingival bacteria and diagnosis of gingivitis and periodontitis. Journal of Dental Research, 1989, vol. 68, pp. 1633-1639.
Clark et al. Ranalexin. A novel antimicrobial peptide from bullfrog (Rana catesbeiana) skin, structurally related to the bacterial antibiotic, polymyxin. The Journal of Biological Chemistry, 1994, vol. 269, pp. 10849-10855.
Corbet et al. The Role of Supragingival Plaque in the Control of Progressive Periodontal-Disease-a Review, Journal of Clinical Periodontology 1993, vol. 20, pp. 307-313.
Creamer et al. Relationship between milk protein polymorphism and physico-chemical properties. Milk Protein Polymorphism: International Dairy Federation Special Issue, 1997, vol. 9702, pp. 110-123.
Cummins et al. Delivery of Antiplaque Agents from Dentifrices, Gels, and Mouthwashes. Journal of Dental Research, 1992, vol. 71, pp. 1439-1449.

(Continued)

*Primary Examiner*—Marianne P Allen
*Assistant Examiner*—Regina M DeBerry
(74) *Attorney, Agent, or Firm*—Paula A. Borden; Bozicevic, Field & Francis LLP

(57) ABSTRACT

The present invention provides antimicrobial peptides. The peptides are non-glycosylated, less than about 100 amino acids in length, and include an amino acid sequence selected from: AVESTVATLEAΣPEVIESPPE (SEQ ID NO:3), AVESTVATLEDΣPEVIESPPE (SEQ ID NO:4), AVESTVATLEASPEVIESPPE (SEQ ID NO:5), AVESTVATLEDSPEVIESPPE (SEQ ID NO:6), DMPIQAFLLYQQPVLG-PVR (SEQ ID NO:7), and conservative substitutions therein. These peptides can be produced synthetically; however, they can most conveniently be derived from casein.

25 Claims, 6 Drawing Sheets

OTHER PUBLICATIONS

Figure 1:
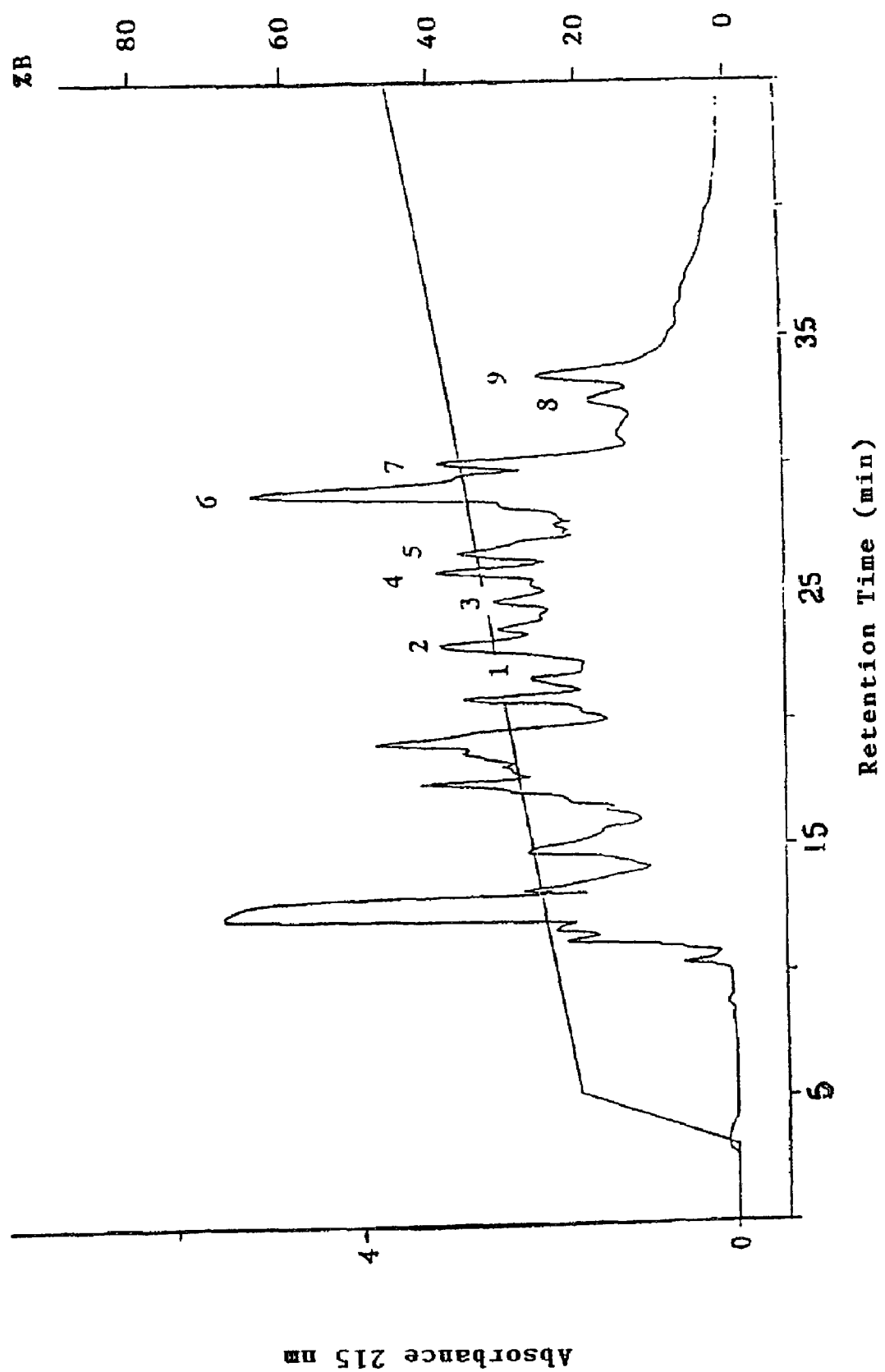

Eldridge et al. Efficacy of an alcohol-free chlorhexidine mouthrinse as an antimicrobial agent. Journal of Prosthetic Dentistry, 1998, vol. 80, pp. 685-690.

Folch et al. A Simple Method for the Isolation and Purification of Total Lipides from Animal Tissues. The Journal of Biological Chemistry, 1957, vol. 226, pp. 497- 509.

Giertesen et al. Inhibition of plaque formation and plaque acidogenicity by zinc and chlorhexidine combinations. Scandinavian Journal of Dental Research, 1998, vol. 96, pp. 541-550.

Goumon et al. The C-terminal bisphosphorylated proenkephalin-A-(209-237)-peptide from adrenal medullary chromaffin granules possesses antibacterial activity. European Journal of Biochemistry, 1996, vol. 235, pp. 516-525.

Hogg. Chemical control of plaque. Dental Update, 1990, vol. 17, pp. 332-334.

Hope et al. Measuring the thickness of an outer layer of viable bacteria in an oral biofilm by viability mapping. Journal of Microbiological Methods, 2003, vol. 54, pp. 403-410.

Loe. The Gingival Index, the plaque index and the retention index systems. Journal of Periodontology, 1976, vol. 38, pp. 610-616.

Malkoski et al. Kappacin, a novel antibacterial peptide from bovine milk. Antimicrobial Agents and Chemotherapy, 2001, vol. 45, pp. 2309-2315.

Marsh. Dentifrices containing new agents for the control of plaque and gingivitis: microbiological aspects. Journal of Clinical Periodontology 1991, vol. 18, pp. 462-467.

Migliore-Samour et al. Biologically active casein peptides implicated in immunomodulation. Journal of Dairy Research, 1989, vol. 56, pp. 357-362.

Moore et al. Bacteriology of human gingivitis. Journal of Dental Research, 1987, vol. 66, pp. 989-995.

Mor et al. Isolation and structure of novel defensive peptides from frog skin. European Journal of Biochemistry, 1994, vol. 219, pp. 145-154.

Nikaido et al. Identification and Characterization of Porins in Pseudomonas-Aeruginosa. Journal of Biological Chemistry, 1991, vol. 266, pp. 770-779.

Plowman et al. Solution conformation of a peptide corresponding to bovine kappa-casein B residues 130-153 by circular dichroism spectroscopy and H-1-nuclear magnetic resonance spectroscopy. Journal of Dairy Research, 1997, vol. 64, pp. 377-397.

Rogers et al. The utilisation of casein and amino acids by Streptococcus sanguis P4A7in continuous culture. Journal of General Microbiology. 1990, vol. 136, pp. 2545-2550.

Romeo D et al. Structure and bactericidal activity of an antibiotic dodecapeptide purified from bovine neutophils. The Journal of Biological Chemistry, 1988, vol. 263, pp. 9573-9575.

Shu et al. Role of urease enzymes in stability of a 10-species oral biofilm consortium cultivated in a constant-depth film fermenter. Infection and Immunity , 2003, vol. 71, pp. 7188-7192.

Simmaco et al. A family of bombinin-related peptides from the skin of Bombina variegata. European Journal of Biochemistry, 1991, vol. 199, pp. 217-222.

Smallcombe et al. WET solvent suppression and its applications to LC NMR and high-resolution NMR spectroscopy. Journal of Magnetic Resonance Series A, 1995, vol. 117, pp. 295-303.

Smith et al. Structural features of bovine caseinomacropeptide A and B by H-1 nuclear magnetic resonance spectroscopy. Journal of Dairy Research, 2002, vol. 69, pp. 85-94.

Spencer et al. A socio-dental study of adult periodontal health: Melbourne 1985. Community Dental Health Monograph No. 5, 1985, Melbourne University Press. pp. 1-142.

Strub et al. Antibacterial activity of glycosylated and phosphorylated chromogranin A-derived peptide 173-194 from bovine adrenal medullary chromaffin granules. Journal of Biological Chemistry, 1996, vol. 271, pp. 28533-28540.

Svedberg, et al. Demonstration of B-casomorphin immunoreactive materials in in vivo digests of bovine milk and in small intestine contents after bovine milk ingestion in adult humans. Peptides, 1985, vol. 6, pp. 825-830.

Talbo et al. Maldi-PSD-MS analysis of the phosphorylation sites of caseinomacropeptide. Peptides, 2001, vol. 22, pp. 1093-1098.

Wilson. Susceptibility of oral bacterial biofilms to antimicrobial agents. Journal of Medical Microbiology, 1996, vol. 44, pp. 79-87.

Wimpenny et al. Modeling spatial gradients. Structure and function of biofilms (W. Characklis and P. Wlderer (ed.)), 1989, pp. 111-127, John Wiley and Sons, Chichester.

Zanetti et al. Molecular cloning and chemical synthesis of a novel antibacterial peptide derived from pig myeloid cells. The Journal of Biological Chemistry, 1994, vol. 269, pp. 7855-7858.

Zucht et al. Casocidin-I: a casein-alpha s2 derived peptide exhibits antibacterial activity. FEBS Letters. 1995, vol. 25,372 (2-3), pp. 185-188.

Boman, et al. Antibacterial Peptides:Key components needed in immunity. Cell, (1991), vol. 65, pp. 205-207.

Jelen. Nordic Milk Protein Conference. Trend in Food Science & Technology, (1996), vol. 7, pp. 171-173.

Lahov and Regelson. Antibacterial and Immunostimulating Casein-derived Substances from Milk: Casecidin, Isracidin Peptites. Fd Chem. Toxic, (1996), vol. 34, No. 1, pp. 131-145.

Yvon, et al. Effects of Caseinomacropeptide (CMP) on Digestion Regulation. Reprod Nutr Dev (1994), vol. 34, pp. 527-537.

* cited by examiner

ANTIMICROBIAL PEPTIDES

CROSS REFERENCE

This application is a continuation of U.S. patent application Ser. No. 09/554,997, filed Aug. 9, 2002, which is a national phase filing under 35 U.S.C. 371 of International Patent Application No. PCT/AU98,00972, filed Nov. 24, 1998, which was published under PCT Article 21(2) on Jun. 3, 1999 in English as WO 99/26971, which application claims the benefit of Australian Patent Application No. PP0514, filed Nov. 23, 1997, each of which applications is incorporated herein by reference.

FIELD OF THE INVENTION

The present invention relates to novel antimicrobial peptides which can be obtained from the milk protein casein or chemically synthesised or produced by recombinant DNA technology. These peptides can be used in foods as antimicrobial preservatives, in oral care products (eg. toothpaste, mouthwash, dental floss) for the control of dental plaque and suppression of pathogens associated with dental caries and periodontal diseases. The antimicrobial peptides may also be used in pharmaceutical preparations for topical or parenteral application or oral administration for the control of oro-pharangeal and gastrointestinal pathogens as well as systemic or localised infections.

BACKGROUND OF THE INVENTION

Periodontal diseases are bacterial-associated inflammatory diseases of the supporting tissues of the teeth and are a major public health problem. Nearly all of the human population is affected by periodontal diseases to some degree. In a recent Melbourne survey (Spencer et al., 1985) only 20% of the adult dentate sample did not require periodontal treatment while 62% required intermediate treatment and 18% required complex treatment. Brown et al. (1989), from an extensive US Dental Health survey reported that only 15% of the studied population was free of periodontal diseases. The major form of periodontal disease is gingivitis which is associated with the non-specific accumulation of dental plaque at the gingival margin. In contrast, the less prevalent, destructive form of periodontal disease (periodontitis) is associated with a sub-gingival infection of specific Gram-negative bacteria. Periodontitis is a major cause of tooth loss in Australian adults.

Although gingivitis may not be a necessary precondition for the development of periodontitis (Christersson et al., 1989) gingivitis is likely to predispose susceptible sites to more serious forms of periodontal disease since the specific Gram-negative bacteria that predominate in periodontitis, but which are not detectable in the healthy periodontium, have been found in low proportions in gingivitis (Moore et al., 1987). Further, the environmental conditions that develop during gingivitis are likely to favour the subsequent colonisation or growth of the species implicated in periodontitis. The control of supragingival plaque is therefore considered an important part of a preventive strategy for the control of periodontal diseases and in fact various plaque control programs have proven to be successful in the prevention of periodontal diseases (Loesche, 1976). In the majority of individuals the customary oral hygiene method of toothbrushing is usually insufficient by itself over long periods to provide a level of plaque control compatible with oral health. Consequently the incorporation of antimicrobial agents into dental products as an aid to controlling dental plaque and gingivitis has been advocated (Addy, 1988; Marsh, 1991) and is of considerable interest to toothpaste and mouthwash companies. A number of agents have been suggested as antiplaque toothpaste additives (eg. bisbiguanides, phenols, metal ions, quartenary ammonium salts) but have either negligible intra-oral activity, undesirable side-effects (eg. mucosal irritation, tooth discolouration) and/or an incompatibility with toothpaste formulations. Triclosan (2,4,4'-trichloro-2'-hydroxy diphenyl ether) an antimicrobial agent used extensively in deodorants, soaps and other dermatological preparations is currently being used as an anti-plaque toothpaste additive in some countries however there is considerable interest to find a clinically efficacious, safe and natural antiplaque agent.

Antimicrobial peptides are widely distributed in nature and play a role in the host defence of plants and animals (Boman and Hultmark, 1987; Bevins and Zasloff, 1990). They include amongst others, the amphipathic channel forming peptides, for example the cecropins isolated from the cecropia moth (Boman and Hultmark, 1987), the magainins isolated from skin secretions of the African clawed frog *Xenopus laevis* (Bevins and Zasloff, 1990), the dermaseptins isolated from the skin of the arboreal frog (Mor and Nicolas, 1994) and the bombinins from the skin of *Bombina variegata* (Simmnaco et al., 1991). Other antimicrobial peptides include the cyclic cationic peptides containing an intramolecular disulphide, for example ranalexin from bullfrog skin (Clark et al., 1994) and bactenecin from bovine neutrophils (Romeo et al., 1988). Proline-containing antimicrobial peptides also have been identified and these include the apidaecins from the lymph fluid of the honeybee (Casteels et al., 1989) and the pig myeloid antimicrobial peptide PMAP-23 (Zanetti et al., 1994).

It is now well established that the milk protein casein should be considered not only as a nutrient but also as a protecting agent against bacterial infection of the neonate mucosa as specific peptides released by tryptic or in situ digestion have been shown to possess marked biological activity. These bioactive peptides are relatively resistant to further proteolytic breakdown and have been detected in the distal portion of the small intestine and blood of humans after ingestion of cow's milk (Svedberg et al., 1985). Migliore-Samour et al. (1989) have shown that peptides β-casein (63-68) PGPIPN (SEQ ID NO:1) and $\alpha_{s1}$-casein (194-199) TTMPLW (SEQ ID NO:2) at concentrations as low as 0.1 µM exert a significant protective effect in mice against *Klebsiella pneumoniae* infection when injected intravenously at 0.3 nag/kg, before lethal infectious challenge. An antibacterial peptide from bovine $\alpha_{a2}$-casein ($\alpha_{s2}$-casein (f172-203)) released by treatment of milk with glacial acetic acid has recently been characterised and shown to inhibit the growth of *Escherichia coli* and *Staphylococuus carnosus* (Zucht et al., 1995).

Antimicrobial peptides having activity against a range of Gram-positive and Gram-negative bacteria have potential in the area of oral care, functional foods, food preservatives and pharmaceuticals. Oral care products include toothpaste, mouthwash, dental floss and professionally applied materials. Functional foods include chewing gum, confectionery, breakfast cereals, infant formula, beverages, lozenges etc. Food preservatives application could include dairy products, soups, salad dressings, processed meats, baked goods, sauces etc. Pharmaceutical use would include systemic and topically applied antibiotics and anti-infectives and medications for the treatment of ulcers and other gastro-intestinal tract diseases.

For food applications, natural antimicrobials are typically used for the maintenance and extension of shelf-life in sauces, wet salads, baked goods and pastries, processed meats, refrigerated dairy products, salad dressings and soaps. Nisin has limited application as a food preservative due to a relatively narrow spectrum of antimicrobial activity and high cost. Food manufacturers using casein antimicrobial peptides as a preservative may use "all natural" label claims which are not allowed when using artificial or chemical preservatives. A major trend in the food industry is the increasing demand for low fat products which in general tend to have increased moisture levels. This creates a demand for better food preservation systems such as the incorporation of natural antimicrobials.

The global market for medications for wound healing, treatment of upper gut ulcers and inflammatory based disease represents a major pharmaceutical market. Clinicians working in the area of duodenal and gastric ulcers currently focus on the bacterium *Helicobacter pylori* as the causative agent in upper gut ulcers. Channel forming antimicrobial peptides that allow $H^+$ to enter the bacterial cell have the potential for treatment of *H. pylori* infections by enhancing the sensitivity of the bacterium to the acid secretions of the stomach.

SUMMARY OF THE INVENTION

The present inventors have developed new peptides which have antimicrobial activity. These peptides can be produced synthetically, however, they can most conveniently be derived from casein.

Accordingly, in a first aspect the present invention consists in an antimicrobial peptide, the peptide being non-glycosylated, less than about 100 amino acids, preferably less than about 70 amino acids, and including an amino acid sequence selected from the group consisting of:—

AVESTVATLEASPEVIESPPE, (SEQ ID NO:3), wherein serine at amino acid residue 12 of SEQ ID NO:3 is a phosphoseryl residue;

AVESTVATLEDSPEVIESPPE, (SEQ ID NO:4), wherein serine at amino acid residue 12 of SEQ ID NO:4 is a phosphoseryl residue;

AVESTVATLEASPEVIESPPE, (SEQ ID NO:5)

AVESTVATLEDSPEVIESPPE, (SEQ ID NO:6)

DMPIQAFLLYQQPVLGPVR, (SEQ ID NO:7)

and conservative substitutions therein.

In a preferred embodiment of the present invention the peptide includes an amino acid sequence selected from the group consisting of:

AVESTVATLEASPEVIESPPE, (SEQ ID NO:3), wherein serine at amino acid residue 12 of SEQ ID NO:3 is a phosphoseryl residue, AVESTVATLEDSPEVIESPPE, (SEQ ID NO:4), wherein serine at amino acid residue 12 of SEQ ID NO:4 is a phosphoseryl residue, AVESTVATLEASPEVIESPPE (SEQ ID NO:5), AVESTVATLEDSPEVIESPPE (SEQ ID NO:6), and DMPIQAFLLYQQPVLGPVR (SEQ ID NO:7), preferably AVESTVATLEASPEVIESPPE, (SEQ ID NO:3), wherein serine at amino acid residue 12 of SEQ ID NO:3 is a phosphoseryl residue, AVESTVATLEDSPEVIESPPE, (SEQ ID NO:4), wherein serine at amino acid residue 12 of SEQ ID NO:4 is a phosphoseryl residue, or DMPIQAFLLYQQPVLGPVR (SEQ ID NO:7).

In a further preferred embodiment of the present invention the peptide includes an amino acid sequence selected from the group consisting of:

MAIPPKKNQDKTEIPTINTIASGEPTSTPTIEAVESTVATLEASPEVIESPPETNTVQVTSTA V (SEQ ID NO:8), wherein serine at amino acid residue 44 of SEQ ID NO:8 is a phosphoseryl residue;

MAIPPKKNQDKTEIPTINTIASGEPTSTPTIEAVESTVATLEASPEVIESPPEINTVQVTSTA V (SEQ ID NO:9), wherein serine at amino acid residue 22 and amino acid residue 44 of SEQ ID NO:9 are phosphoseryl residues;

MAIPPKKNQDKTEIPTINTIASGEPTSTPTTEAVESTVATLEDSPEVIESPPEINTVQVTSTA V (SEQ ID NO: 10), wherein serine at amino acid residue 44 of SEQ ID NO:10 is a phosphoseryl residue;

MAIPPKKNQDKTEIPTINTIASGEPTSTPTTEAVESTVATLEDSPEVIESPPEINTVQVTSTA V (SEQ ID NO: 11), wherein serine at amino acid residue 22 and amino acid residue 44 of SEQ ID NO:11 are phosphoseryl residues;

TEIPTINTIASGEPTSTPTIEAVESTVATLEASPEVIESPPEINTVQVTSTAV (SEQ ID NO:12), wherein serine at amino acid residue 33 of SEQ ID NO:12 is a phosphoseryl residue;

TEIPTINTIASGEPTSTPTIEAVESTVATLEASPEVIESPPEINTVQVTSTAV (SEQ ID NO:13), wherein serine at amino acid residue 11 and serine at amino acid residue 33 of SEQ ID NO:13 are phosphoseryl residues;

TEIPTINTIASGEPTSTPTTEAVESTVATLEDSPEVIESPPETNTVQVTSTAV (SEQ ID NO:14), wherein serine at amino acid residue 33 of SEQ ID NO:14 is a phosphoseryl residue;

TEIPTINTIASGEPTSTPTTEAVESTVATLEDSPEVIESPPEINTVQVTSTAV (SEQ ID NO: 15), wherein serine at amino acid residue 11 and serine at amino acid residue 33 of SEQ ID NO:15 are phosphoseryl residues;

MAIPPKKNQDKTEIPTINTIASGEPTSTPTIEAVESTVATLEASPEVIESPPEINTVQVTSTAV (SEQ ID NO:16);

MAIPPKKNQDKTEIPTINTIASGEPTSTPTTEAVESTVATLEDSPEVIESPPEINTVQVTSTAV (SEQ ID NO:17);

TEIPTINTIASGEPTSTPTIEAVESTVATLEASPEVIESPPEINTVQVTSTAV (SEQ ID NO:18);

TEIPTINTIASGEPTSTPTTEAVESTVATLEDSPEVIESPPEINTVQVTSTAV (SEQ ID NO:19);

It is further preferred that the peptide includes an amino acid sequence selected from the group consisting of:—

MAIPPKKNQDKTEIPTINTIASGEPTSTPTIEAVESTVATLEASPEVIESPPEINTVOVTSTA V (SEQ ID NO:8), wherein serine at amino acid residue 44 of SEQ ID NO:8 is a phosphoseryl residue;

MAIPPKKNQDKTEIPTINTIASGEPTSTPTIEAVESTVATLEASPEVIESPPEINTVQVTSTA V (SEQ ID NO:9), wherein serine at amino acid residue 22 and amino acid residue 44 of SEQ ID NO:9 are phosphoseryl residues;

MAIPPKKNQDKTEIPTJNTIASGEPTSTPTTEAVESTVATLEDSPEVJESPPEINTVOVTSTA V (SEQ ID NO:10), wherein serine at amino acid residue 44 of SEQ ID NO:10 is a phosphoseryl residue;

MAIPPKKNQDKTEIPTINTIASGEPTSTPTTEAVESTVATLEDSPEVIESPPEINTVQVTSTA V (SEQ ID NO: 11), wherein serine at amino acid residue 22 and amino acid residue 44 of SEQ ID NO:11 are phosphoseryl residues;

TEIPTINTIASGEPTSTPTIEAVESTVATLEASPEVIESPPEJNTVQVTSTAV (SEQ ID NO:12), wherein serine at amino acid residue 33 of SEQ ID NO:12 is a phosphoseryl residue;

TEIPTINTIASGEPTSTPTIEAVEST-
VATLEASPEVIESPPEINTVOVTSTAV (SEQ ID NO:13),
wherein serine at amino acid residue 11 and serine at amino
acid residue 33 of SEQ ID NO:13 are phosphoseryl residues;
TEIPTINTIASGEPTSTPTTEAVEST-
VATLEDSPEVIESPPEINTVQVTSTAV (SEQ ID NO:14),
wherein serine at amino acid residue 33 of SEQ ID NO:14 is
a phosphoseryl residue;
TEIPTINTIASGEPTSTPTTEAVEST-
VATLEDSPEVIESPPEINTVQVTSTAV (SEQ ID NO:15),
wherein serine at amino acid residue 11 and serine at amino
acid residue 33 of SEQ ID NO:15 are phosphoseryl residues;
MAIPPKKNQDKTEIPTINTIASGEPT-
STPTIEAVESTVATLEASPEVIESPPEINTVQVTSTAV
(SEQ ID NO:16);
MAIPPKKNQDKTEIPTINTIASGEPT-
STPTTEAVESTVATLEDSPEVIESPPEINTVQVTSTAV
(SEQ ID NO:17);
TEIPTINTIASGEPTSTPTIEAVEST-
VATLEASPEVIESPPENTVQVTSTAV (SEQ ID NO:18);
and
TEIPTIINTIASGEPTSTPTTEAVEST-
VATLEDSPEVIESPPEINTVQVTSTAV (SEQ ID NO:19).

In yet a further preferred embodiment of the present invention the peptide is selected from the group consisting of:—
MAIPPKKNODKTEIPTINTIASGEPT-
STPTIEAVESTVATLEASPEVIESPPEINTVQVTSTA V
(SEQ ID NO:8), wherein serine at amino acid residue 44 of
SEQ ID NO:8 is a phosphoseryl residue;
MAIPPKKNQDKTEIPTINTIASGEPT-
STPTIEAVESTVATLEASPEVIESPPEINTVQVTSTA V
(SEQ ID NO:9), wherein serine at amino acid residue 22 and
amino acid residue 44 of SEQ ID NO:9 are phosphoseryl
residues;
MAIPPKKNODKTEIPTTNTIASGEPT-
STPTTEAVESTVATLEDSPEVIESPPEINTVQVTSTA V
(SEQ ID NO:10), wherein serine at amino acid residue 44 of
SEQ ID NO:10 is a phosphoseryl residue;
MAIPPKKNQDKTEIPTINTIASGEPT-
STPTTEAVESTVATLEDSPEVIESPPEINTVQVTSTA V
(SEQ ID NO:11), wherein serine at amino acid residue 22 and
amino acid residue 44 of SEQ ID NO:11 are phosphoseryl
residues;
TEIPTJNTIASGEPTSTPTIEAVEST-
VATLEASPEVIESPPEINTVQVTSTAV (SEQ ID NO:12,
wherein serine at amino acid residue 33 of SEQ ID NO:12 is
a phosphoseryl residue;
TEIPTINTIASGEPTSTPTIEAVEST-
VATLEASPEVIESPPETNTVOVTSTAV (SEQ ID NO:13),
wherein serine at amino acid residue 11 and serine at amino
acid residue 33 of SEQ ID NO:13 are phosphoseryl residues;
TEIPTINTIASGEPTSTPTTEAVEST-
VATLEDSPEVIESPPEJNTVOVTSTAV (SEQ ID NO:14),
wherein serine at amino acid residue 33 of SEQ ID NO:14 is
a phosphoseryl residue;
TEIPTINTIASGEPTSTPTTEAVEST-
VATLEDSPEVIESPPEINTVQVTSTAV (SEQ ID NO:15),
wherein serine at amino acid residue 11 and serine at amino
acid residue 33 of SEQ ID NO:15 are phosphoseryl residues;
AVESTVATLEASPEVIESPPE, (SEQ ID NO:3), wherein
serine at amino acid residue 12 of SEQ ID NO:3 is a phosphoseryl residue,
AVESTVATLEDSPEVIESPPE, (SEQ ID NO:4), wherein
serine at amino acid residue 12 of SEQ ID NO:4 is a phosphoseryl residue;
MAIPPKKNQDKTEIPTINTIASGEPT-
STPTIEAVESTVATLEASPEVIESPPEINTVQVTSTAV
(SEQ ID NO:16);
MAIPPKKNQDKTEIPTINTIASGEPT-
STPTTEAVESTVATLEDSPEVIESPPETNTVQVTSTAV
(SEQ ID NO:17);
TEIPTINTIASGEPTSTPTIEAVEST-
VATLEASPEVIESPPEINTVQVTSTAV (SEQ ID NO:18);
TEIPTINTIASGEPTSTPTTEAVEST-
VATLEDSPEVIESPPEINTVQVTSTAV (SEQ ID NO:19);
AVESTVATLEASPEVIESPPE (SEQ ID NO:5);
AVESTVATLEDSPEVIESPPE (SEQ ID NO:6); and
DMPIQAFLLYQQPVLGPVR (SEQ ID NO:7).

As will be understood by those skilled in this field the peptide of the present invention can be conjugated to other molecules, such as acyl derivatives, to alter the delivery profile or pharmacokinetics of the peptide. Such conjugates are described in PCT/AU90/00599, the disclosure of which is incorporated herein by reference, and which discloses compounds in which peptides, amino acids or derivatives thereof are bound to other molecules, in particular fatty acids, which facilitate the use of such peptides, amino acids or derivatives thereof.

In a second aspect the present invention consists in a chimeric compound, the compound including the peptide of the first aspect of the present invention conjugated to a non-peptide molecule. It is preferred that the non-peptide molecule includes acyl groups.

In a third aspect the invention provides an antimicrobial compositions including the peptide of the first aspect of the present invention together with a pharmaceutically-acceptable carrier. Such compositions may be dental, intra-oral compositions, therapeutic anti-infective compositions for topical and systemic application. Dental compositions or therapeutic compositions may be in the form of a gel, liquid, solid, powder, cream or lozenge. Therapeutic compositions may also be in the form of tablets or capsules.

In a fourth aspect, there is provided a method of treating or preventing dental caries or periodontal disease in a subject, the method comprising the step of administering a peptide or composition of the present invention to the teeth or gums of a subject in need of such treatments. Topical administration of the peptide is preferred.

Without wishing to be bound by scientific theory it is believed that the peptides of the present invention exert their antimicrobial activity by virtue of their amphipathic nature. It is believed that the peptides are incorporated into the bacterial membrane where they form aggregates. These aggregates provide or form pores or channels through the membrane through which ions may pass. The uncontrolled passage of ions across the bacterial membrane results in the death of the bacterial cell.

As it is the physical nature of the peptides rather than the specific sequence of the peptide which results in their antimicrobial activity so called conservative substitutions may be made in the peptide sequence with no substantial loss of activity. It is intended that such conservative substitutions which do not result in a substantial loss of activity are encompassed in the present invention.

Whilst the concept of conservative substitution is well understood by the person skilled in the art, for the sake of clarity conservative substitutions are those set out below.
G, A, V, I, L, M;
D, E, S;
N, Q;
S, T;
K, R, H;

F, Y, W, H; and
P, Nα-alkalamino acids.

Where Σ is a phosphoseryl residue.

The peptides of the present invention have a number of applications, for example, they can be used in foods as antimicrobial preservatives, in oral care products (toothpastes and mouthrinses) for the control of dental plaque and suppression of pathogens associated with dental caries and periodontal diseases. The antimicrobial peptides of the present invention may also be used in pharmaceutical preparations (eg, topical and systemic anti-infective medicines).

Throughout this specification the word "comprise", or variations such as "comprises" or "comprising", will be understood to imply the inclusion of a stated element or integer or group of elements or integers but not the exclusion of any other element or integer or group of elements or integers.

DETAILED DESCRIPTION OF THE INVENTION

The present invention relates to the novel antimicrobial peptides. These peptides were initially derived from casern, κ-casein (106-169) (SEQ ID NO:16, 17) and β-casein (184-202) (SEQ ID NO:7) [Table 1]. These peptides have potential to be uked for the following micro-organisms inter alia.

*Streptococcus mutans*
*Staphylococcus aureus*
*Streptococcus sanguinis*
*Escherichia coli*
*Salmonella typhimurium*
*Pseudomonas aeruginosa*
*Porphyromonas gingivalis*
*Campylobacter jejuni*
*Listeria monocytogenes*
*Helicobacter pylori*
*Clostridium botulinum*
*Streptococcus pyogenes*
*Streptococcus pneumoniae*
*Candida albicans*

The antimicrobial peptides Ser(P)$^{149}$ κ-casein B (106-169) (SEQ ID NO:8) and Ser(P)$^{149}$ κ-casein B (117-169) (SEQ ID NO: 12) both had a minimum inhibitory concentration (MIC) of 2.4 μM against the oral pathogens *Streptococcus mutans* and *Streptococcus sobrinus* and at a ten-fold lower concentration (0.24 μM) inhibited growth of these bacteria by 41%.

The antimicrobial peptides Ser(P)$^{149}$ κ-casein (117-169) (SEQ ID NO:12) and Ser(P)$^{127}$ Ser(P)$^{149}$ κ-casein (117-169) (SEQ ID NO:13) and β-casein (184-202) (SEQ ID NO:7) can be purified from a tryptic digest of bovine casein using standard chromatographic procedures of anion exchange and reversed-phase chromatography (HPLC). Ser(P)$^{149}$ κ-casein (106-169) (SEQ ID NO:8) and Ser(P)$^{127}$, Ser(P)$^{149}$ κ-casein (106-169) (SEQ ID NO:11) can also be prepared from cheese whey and rennet whey by removal of the whey proteins by ultrafiltration, or acid precipitation followed by reversed-phase HPLC purification of the phosphopeptides. The peptides can be prepared from casein of other species, eg. goat, sheep etc.

TABLE 1

Casein Antimicrobial Peptides

| Peptide | Sequence$^a$ |
|---|---|
| Ser(P)$^{149}$ κ-casein B (106-169) | MAIPPKKNQDKTEIPTINTIASGEPTSTPTIEAVESTVA TLEASPEVIESPPEINTVQVTSTAV (SEQ ID NO:8), wherein serine at amino acid residue 44 of SEQ ID NO:8 is a phosphoseryl residue |
| Ser(P)$^{127}$, Ser(P)$^{149}$ κ-casein B (106-169) | MAIPPKKNQDKTEIPTINTIASGEPTSTPTIEAVESTVA TLEASPEVIESPPEINTVQVTSTAV (SEQ ID NO:9), wherein serine at amino acid residue 22 and amino acid residue 44 of SEQ ID NO:9 are phosphoseryl residues |
| Ser(P)$^{149}$, κ-casein A (106-169) | MAIPPKKNQDKTEIPTINTIASGEPTSTPTTEAVESTVA TLEDSPEVIESPPEINTVQVTSTAV (SEQ ID NO:10), wherein serine at amino acid residue 44 of SEQ ID NO:10 is a phosphoseryl residue |
| Ser(P)$^{127}$, Ser(P)$^{149}$ κ-Caein A (106-169) | MAIPPKKNQDKTEIPTINTIASGEPTSTPTTEAVESTVA TLEDSPEVIESPPEINTVQVTSTAV (SEQ ID NO:11), wherein serine at amino acid residue 22 and amino acid residue 44 of SEQ ID NO:11 are phosphoseryl residues |
| Ser(P)$^{149}$ κ-casein B (117-169) | TEIPTINTIASGEPTSTPTIEAVESTVATLEASPEVIES PPEINTVQVTSTAV (SEQ ID NO:12), wherein serine at amino acid residue 33 of SEQ ID NO:12 is a phosphoseryl residue |
| Ser(P)$^{127}$, Ser(P)$^{149}$ κ-casein B (117-169) | TEIPTINTIASGEPTSTPTIEAVESTVATLEASPEVIES PPEINTVQVTSTAV (SEQ ID NO:13), wherein serine at amino acid residue 11 and serine at amino acid residue 33 of SEQ ID NO:13 are phosphoseryl residues |
| Ser(P)$^{149}$ κ-casein A (117-169) | TEIPTINTIASGEPTSTPTTEAVESTVATLEDSPEVIES PPEINTVQVTSTAV (SEQ ID NO:14), |

TABLE 1-continued

Casein Antimicrobial Peptides

| Peptide | Sequence[a] |
|---|---|
| | wherein serine at amino acid residue 33 of SEQ ID NO:14 is a phosphoseryl residue |
| Ser(P)[127], Ser(P)[149] κ-casein A (117-169) | TEIPTINTIASGEPTSTPTTEAVESTVATLEDSPEVIES PPEINTVQVTSTAV (SEQ ID NO:15), wherein serine at amino acid residue 11 and serine at amino acid residue 33 of SEQ ID NO:15 are phosphoseryl residues |
| Ser(P)[149] κ-casein B (138-158) | AVESTVATLEASPEVIESPPE, (SEQ ID NO:3), wherein serine at amino acid residue 12 of SEQ ID NO:3 is a phosphoseryl residue |
| Ser(P)[149] κ-casein A (138-158) | AVESTVATLEDSPEVIESPPE, (SEQ ID NO:4), wherein serine at amino acid residue 12 of SEQ ID NO:4 is a phosphoseryl residue |
| κ-casein B (106-169) | MAIPPKKNQDKTEIPTINTIASGEPTSTPTIEAVESTVA TLEASPEVIESPPEINTVQVTSTAV (SEQ ID NO:16) |
| κ-casein A (106-169) | MAIPPKKNQDKTEIPTINTIASGEPTSTPTTEAVESTVA TLEDSPEVIESPPEINTVQVTSTAV (SEQ ID NO:17) |
| κ-casein B (117-169) | TEIPTINTIASGEPTSTPTIEAVESTVATLEASPEVIES PPEINTVQVTSTAV (SEQ ID NO:18) |
| κ-casein A (117-169) | TEIPTINTIASGEPTSTPTTEAVESTVATLEDSPEVIES PPEINTVQVTSTAV (SEQ ID NO:19) |
| κ-casein B (138-158) | AVESTVATLEASPEVIESPPE (SEQ ID NO:5) |
| κ-casein A (138-158) | AVESTVATLEADPEVIESPPE (SEQ ID NO:6) |
| β-casein (184-202) | DMPIQAFLLYQQPVLGPVR (SEQ ID NO:7) |

[a]Sequence identified using the one letter amino acid code

The peptide κ-casein (106-169) ((SEQ ID NO:16) and (SEQ ID NO:17)) is present in cheese whey or rennet whey in several different forms. The peptide has two major genetic variants (A (SEQ ID NO:17) and B (SEQ ID NO:16)) and is post-translationally modified by glycosylation and phosphorylation. The glycosylated forms, known as the Kappa-caseino-glycopeptide or glycomacropeptide have been described by Neeser (U.S. Pat. Nos. 4,992,420 and 4,994,441) as anti-plaque and anti-caries agents by virtue of the oligosaccharide chains linked to threonine residues of the peptide. Neeser claims that the oligosaccharide chains of the glycopeptide, by specifically binding to plaque-forming oral bacteria, block the adherence of these bacteria onto salivary-coated tooth enamel. The glycosylated forms of κ-casein (106-169) ((SEQ ID NO:16) and (SEQ ID NO:17)) can be separated from the non-glycosylated forms by chromatography (eg, anion exchange and reversed-phase HPLC) or by selective precipitation or ultrafiltration. Only the non-glycosylated forms of κ-casein (117-169) ((SEQ ID NO:18) and (SEQ ID NO:19)) or κ-casein (106-169) ((SEQ ID NO:16) and (SEQ ID NO:17)) showed antimicrobial activity. As glycosylation destroys antimicrobial activity it is desirable to separate the glyco- and aglyco-forms of κ-casern (117-189) ((SEQ ID NO:18) and (SEQ ID NO:19)) or κ-casein (106-169) ((SEQ ID NO:16) and (SEQ ID NO:17)) which can be achieved using chromatography, selective precipitation or ultrafiltration. Phosphorylation of Ser[149] and to a lesser extent Ser[127] are important for antimicrobial activity and the phosphorylated forms of the two major genetic variants (A (SEQ ID NO:17) and B (SEQ ID NO:16)) appear to possess equal activity (Table 1). The Neeser patents do not disclose the antimicrobial activity of κ-casein (106-169) ((SEQ ID NO:16) and (SEQ ID NO:17)) nor the use of the non-glycosylated forms of the peptide for the suppression of bacterial pathogens.

In a particularly preferred embodiment of the invention, the antimicrobial peptide is incorporated into dentifrices such as toothpaste, mouth washes or formulations for the mouth to aid in the prevention and/or treatment of dental caries and periodontal diseases. The peptide may comprise 0.01-50% by weight of the composition, preferably 0.1-10%. For oral compositions it is preferred that the amount of the peptide administered is 0.01-50% by weight, preferably 0.1-10% by weight of the composition. The oral composition of this invention which contains the above-mentioned peptides may be prepared and used in various forms applicable to the mouth such as dentifrice including toothpastes, toothpowders and liquid dentifrices, mouthwashes, troches, chewing gums, dental pastes, gingival massage creams, gargle tablets, lozenges, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm^2/gm.$, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature which does not denature the antimicrobial peptide of the invention, and it is preferred to employ as the surface-active agent a detersive material which imparts to the composition detersive and foaming properties while not denaturing the peptide. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with peptides are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1-5% by weight. It is noteworthy, that the surface active agent may assist in the dissolving of the peptide of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticisers or softeners, sugar or other sweeteners or such as glucose, sorbitol and the like.

In another embodiment, the peptide of the invention is formulated in foods to act as a preservative preferably comprising 0.01-10% w/w, more preferably 0.1-5% w/w, most preferably 1-5% and particularly 2% w/w.

The present invention provides compositions including pharmaceutical compositions comprising the antimicrobial peptide as described together with a pharmaceutically-acceptable carrier. Such compositions may be selected from the group consisting of dental, intra-oral compositions, therapeutic anti-infective compositions for topical and systemic application. Dental compositions or therapeutic compositions may be in the form of a gel, liquid, solid, powder, cream or lozenge. Therapeutic compositions may also be in the form of tablets or capsules.

The present invention also provides a method of treating or preventing dental caries or periodontal disease comprising the step of administering a peptide or composition of the invention to the teeth or gums of a subject in need of such treatments. Topical administration of the peptide is preferred.

The invention also provides a method of producing the antimicrobial peptide from casein or whey, κ-casein (106-169) ((SEQ ID NO:16) and (SEQ ID NO:17)) can be obtained from cheese or rennet whey by ultrafiltration or acid precipitation. Ultrafiltration of whey through a 10,000-30,000 nominal molecular weight cut off (NMCO) membrane filter at neutral or preferably acidic pH (3-5) retains the majority of whey proteins producing a permeate rich in casein peptides, lactose and minerals. Ultrafiltration and concentration of the permeate using a 1000 NMCO membrane filter produces a fraction rich in κ-casein (106-169) ((SEQ ID NO:16) and (SEQ ID NO:17)). This fraction is then incubated with trypsin and the resulting hydrosylate subjected to reversed-phase HPLC producing a relatively pure κ-casein (117-169) ((SEQ ID NO:18) and (SEQ ID NO:19)) peptide. Alternatively the peptides K-casein (117-169) ((SEQ ID NO:18) and (SEQ ID NO:19)) and β (184-202) (SEQ ID NO:7) can be obtained from a tryptic digest of casein using reversed-phase HPLC. Peptide κ-casein (138-158) ((SEQ ID NO:5) and (SEQ ID NO:6)) can be obtained by a partial endo-Glu-C digest of κ-casein (106-169) ((SEQ ID NO:16) and (SEQ ID NO:17)) followed by purification using reversed-phase HPLC.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

In order that the nature of the present invention may be more clearly understood preferred forms thereof will now be described with reference to the following non-limiting examples.

FIGURE LEGENDS

FIG. 1. Reversed-phase HPLC of a tryptic digest of a Whey Protein Concentrate (WPC). The WPC tryptic digest (8 mg) was applied to a Brownlee RP-300 $C_8$ column. The sample was eluted using a stepwise linear gradient of 0-20% B in 2 min followed by 20-45% B in 40 min at a flow rate of 1 ml/min. Eluant A was 0.1% (v/v) TFA in water and eluant B was 80% (v/v) acetonitrile in 0.1% (v/v) TFA in water.

Figure 2:
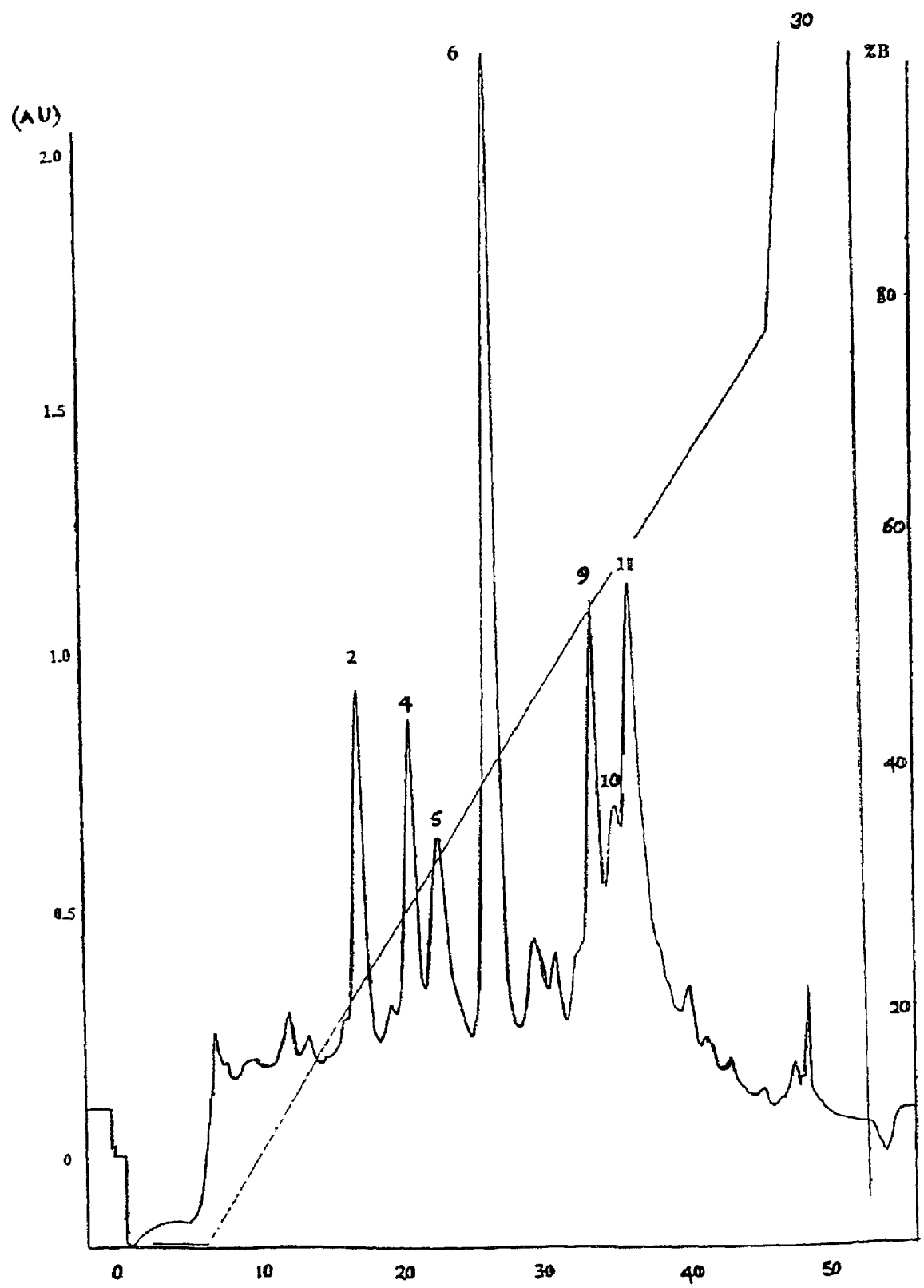

FIG. 2. Anion exchange chromatography of peak 9 from RP-HPLC of the WPC tryptic digest. Peak 9 was applied to a Mono Q column attached to a SMART™ system and eluted using 0-75% elutant B in 40 min at a flow rate of 100 μl/min. Elutant A was 20 mM Tris-HCl pH 8.0, 10 mM KCl and elutant B was 20 mM Tris-HCl pH 8.0, 500 mM KCl.

Figure 3:
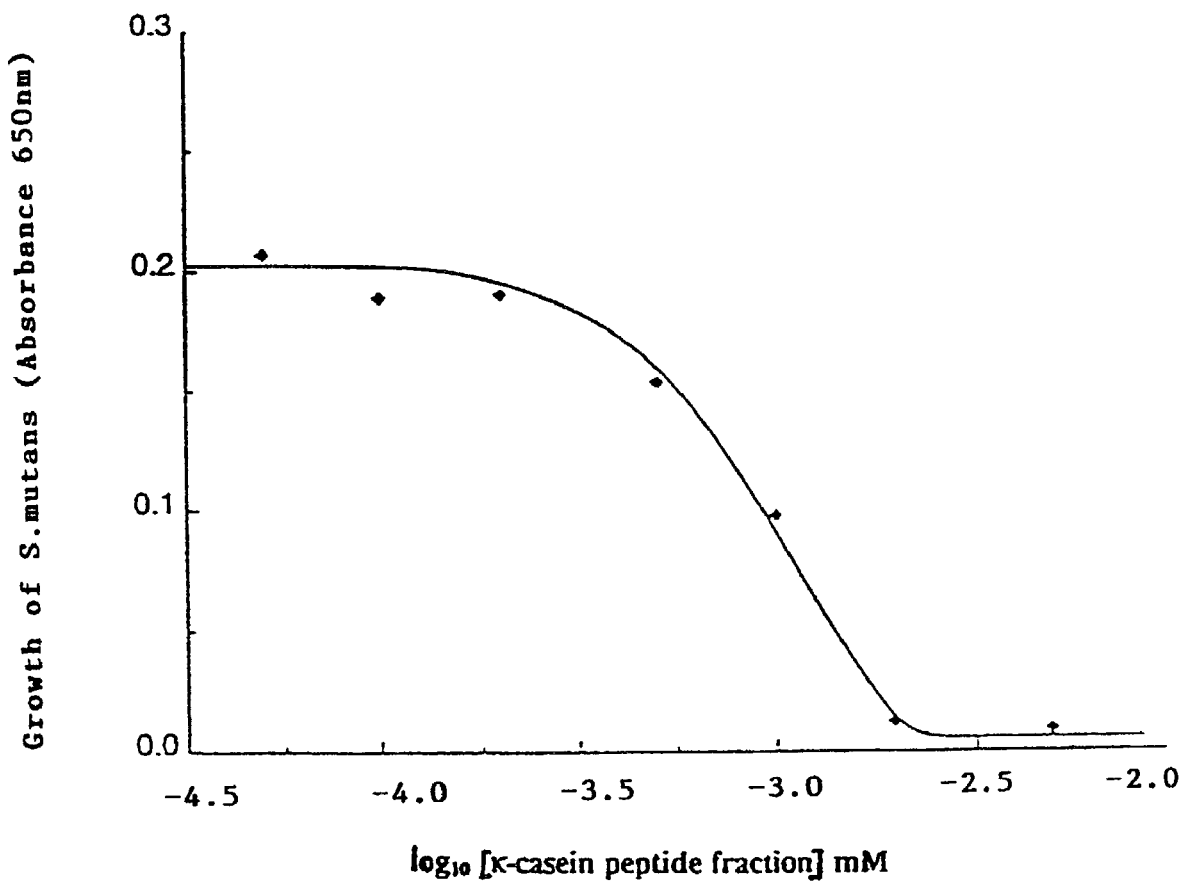

FIG. 3. Determination of the MIC of κ-casein A Ser(P)$^{149}$ (117-169) (SEQ ID NO:14) for *Streptococcus mutans* Ingbritt. The MIC was 2.4 μM.

Figure 4:
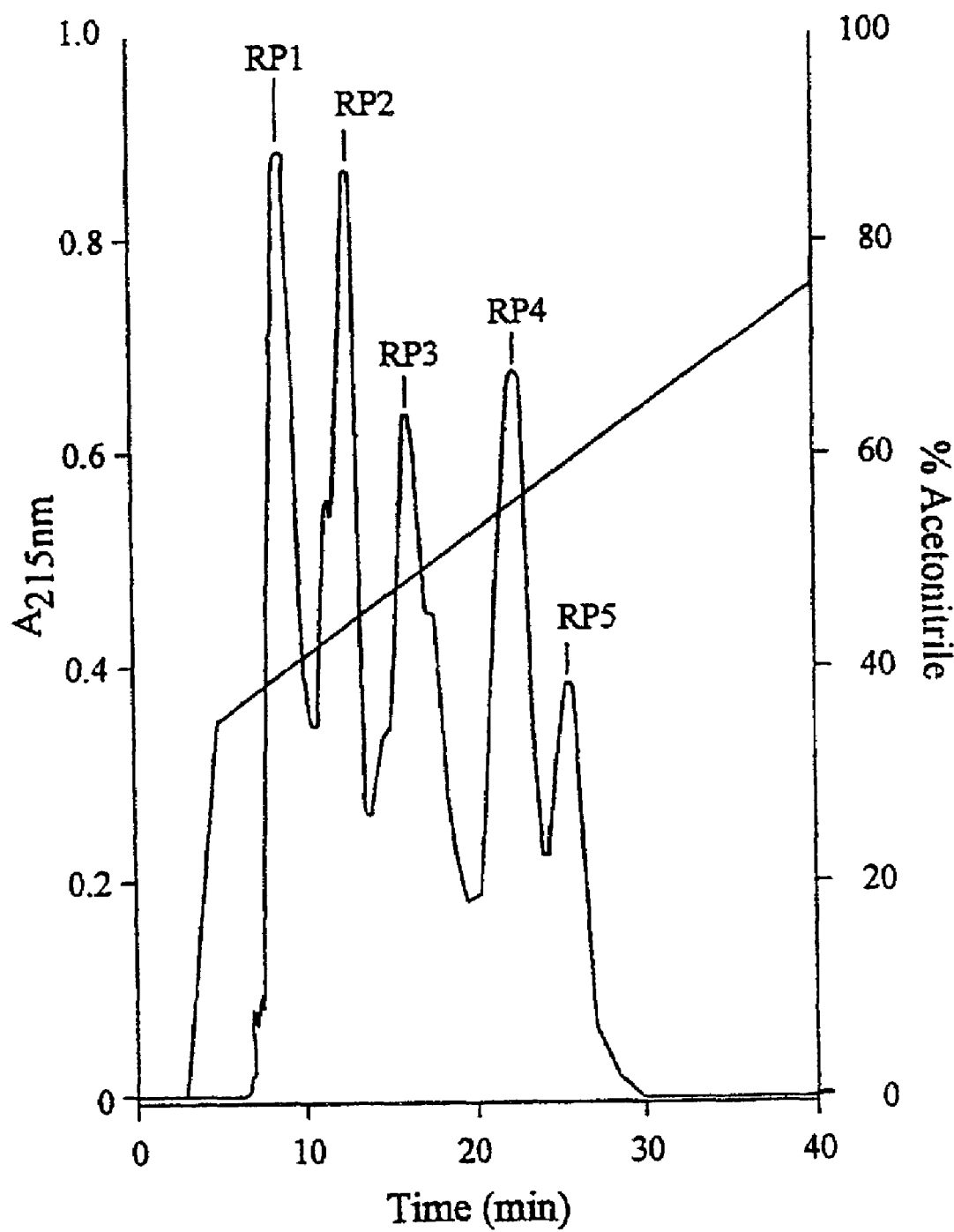

FIG. 4. Analytical reversed-phase HPLC elution profile of UF-whey. A sample of UF-whey was dissolved in solvent A and applied to an analytical column (C18) and then eluted using a linear gradient from 0-35% Solvent B in 5 min followed by 35-80% Solvent B in 40 min at a flow rate of 1.0 ml/min. Solvent A consisted of 0.1% TFA in water and Solvent B contained 90% acetonitrile (v/v/0.1% TFA in water). Peaks were detected at 215 nm, collected manually at 215 nm and lyophilised.

Figure 5:
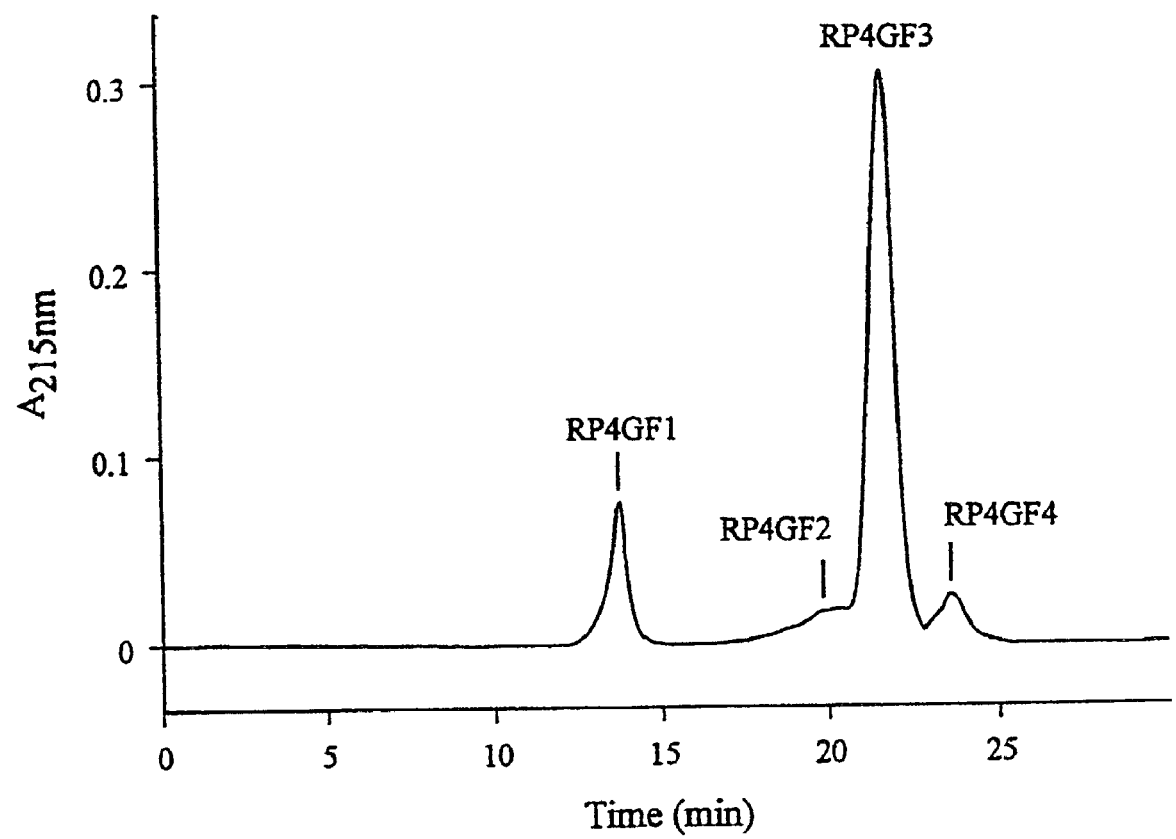

FIG. 5. Purification of peak 4 (from RP-HPLC) using gel filtration. Peak 4 was applied to a gel filtration column connected to an ABI system. Material was eluted using 30% acetonitrile (v/v)/0.1% TFA at a flow rate of 1 ml/min and monitored at 215 nm.

Figure 6:
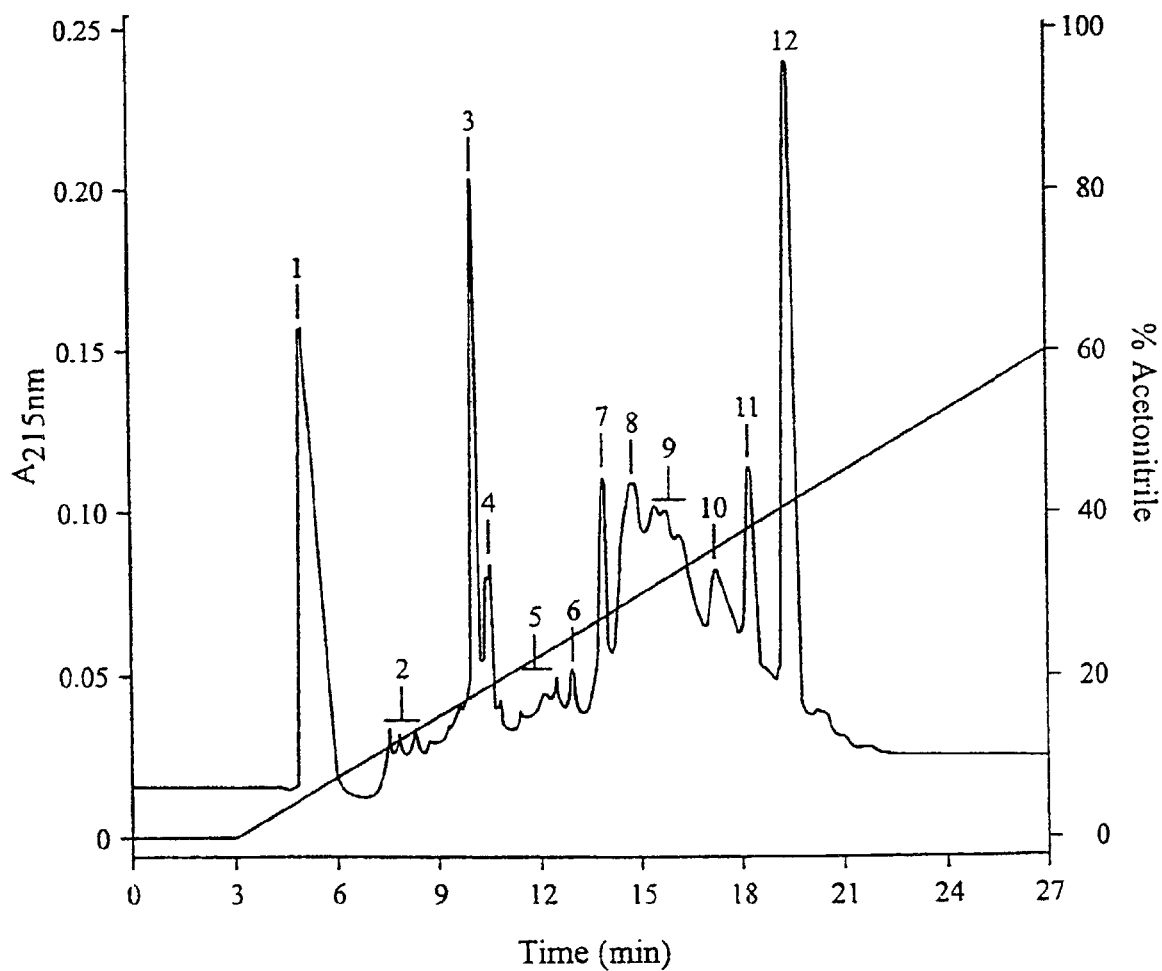

FIG. 6. Purification of peptides generated by the hydrolysis of TCA-soluble UF-whey by endopeptidase Glu-C. A sample was dissolved in Solvent A (0.1% TFA v/v in water) and applied to an analytical column (C18). Peaks were eluted using a gradient of 0-20% Solvent B (90% acetonitrile v/v/0.1% TFA in water) in 4 min followed by 20%-40% Solvent B in 40 min. Peaks were monitored at 215 nm.

Specific examples of formulations containing the antimicrobial peptide of the invention are provided below.

EXAMPLE 1

Preparation of Antimicrobial Peptides from a Tryptic Digest of Whey Protein Concentrate Whey protein concentrate (50 mg/ml) in water (pH 8.0) was hydrolysed using Novo trypsin (1 mg/ml) at 50° C. for 2 h with the pH maintained at 8.00±0.01 by the addition of 1N NaOH. Hydrolysis was terminated by the addition of 1M HCl to pH 4.6. The hydrolysate was centrifuged (11,600 g for 10 min) and then filtered through a 0.2 µm PVDF filter before being applied to a 7 µm $C_8$ (Brownlee) reversed-phase column (4.6×220 mm). The sample was eluted using an Applied Biosystems 140 A Solvent Delivery System to generate a stepwise linear gradient from 0-20% B in 2 min followed by 20-45% B in 40 min at a flow rate of 1 ml/min. Eluant A was 0.1% (v/v) TFA in water and eluant B was 80% (v/v) acetonitrile, 0.1% (v/v) TFA in water. The eluant was monitored using an Applied Biosystems 1000S Diode Array detector at a primary wavelength of 215 nm. The chromatogram obtained is shown in FIG. 1. Peaks were collected and assayed for antimicrobial activity. Antimicrobial assays were carried out in liquid growth medium using sterile 96 well plates, each well having a capacity of 300 µL. The growth medium consisted of Todd Hewit broth (36.4 g/L), Yeast Extract (5.0 g/L) with 100 mmol/L potassium phosphate buffer. Routinely the pH of the growth medium was adjusted to 6.3. An inoculum of approximately $1.5 \times 10^2$ cells (Streptococcus sanguis, Streptococcus mutans, Porphyromonas gingivalis) that had been harvested during the exponential phase of growth, was added to each well. The ionophore gramicidin (40 µmol/L final concentration) was added to a series of wells as a negative control. Positive controls contained only the inoculum and the growth medium. Growth was determined over a 30 hour period after inoculation by measuring the optical density of the cell suspensions at a wavelength of 650 nm ($OD_{650}$), using a microplate reader (Biorad, model 450). Growth was determined by subtracting the initial reading, taken immediately after inoculation from the final reading (maximum culture OD).

Antimicrobial assays were also carried out on agar plates containing suitable growth media that had been inoculated with a lawn of the test bacterial species. Filter paper discs (6 mm diameter), to which was added 50 µL of the peptide solution, were placed on the surface of the agar plate. The diameter of the zone of growth inhibition around each disc was determined after three days of incubation and compared to a control that only had buffer added. Growth conditions depended on the bacterial species being tested, however they were routinely cultured in an anaerobic work station at 37° C. Only peak 9 of FIG. 1 exhibited antimicrobial activity. Analysis of this peak using amino acid sequence analysis (Hewlett Packard automated protein sequencer) and mass analysis (Perseptive Voyager MALDI-TOF mass spectrometer) revealed that the peak was heterogenous and so the sample was subjected to anion exchange chramatography on a Mono Q PC 1.6/5 (10 µm) column attached to a SMART™ (Pharmacia) system. The sample was eluted using a linear gradient from 0-75% B in 40 mm at a flow rate of 100 µl/mm. Eluant A was 20 mM Tris-HCl pH 8.0, 10 mM KCL. Eluant B was 20 mM Tris-HCl pH 8.0, 500 mM KCl. The eluant was monitored at 215 and 280 nm using the µ Peak monitor. The anion exchange chromatogram for peak 9 from RP-HPLC is shown in FIG. 2. Peaks were collected and assayed for antimicrobial activity and only peaks 9, 10 and 11 exhibited activity. N-terminal sequence and mass analyses nevealed that fraction 9 contained Ser(P)$^{149}$ κ-casein A (113-169) (SEQ ID NO:10), fraction 10 contained Ser(P)$^{149}$ κ-casein A (124-169) (SEQ ID NO:10) and fraction 11 contained Ser(P)$^{149}$ κ-casein A (117-169) (SEQ ID NO:14). Mass analysis revealed that none of the peptides were glycosylated. The minimum inhibitory concentration (MIC) of pure Ser(P)$^{149}$ κ-casein A (117-169) (SEQ ID NO:14) was then determined for the bacterium Streptococcus mutans and is shown in FIG. 3. The MIC obtained was 2.4 µM.

EXAMPLE 2

A. Preparation of Antimicrobial Peptides from Cheese Whey

Cheese whey was ultrafiltered (UF) though a 20,000 molecular weight cut off membrane. The filtrate was collected and proteins were precipitated by addition of trichloroacetic acid (TCA) to a final concentration of 11% w/v. Precipitated proteins were removed by centrifugation (10,000 g, 5 min) and the neutralised supernatant was lyophilised. The dried TCA-soluble UF whey was dissolved in 0.1% TFA in water and subjected to RP-HPLC. The sample was applied to a Brownlee aquapore analytical (C18) reversed-phase column (220×4.6 mm) or a Brownlee (C18) preparative column (25 cm×10 mm). Solvent B consisted of 90% acetonitrile containing 0.1% v/v TFA and solvent A consisted of 0.1% TFA in water. The eluant was monitored using an Applied Biosystems Incorporated (ABI; Melbourne, Vic., Australia) 1000S diode array detector at a wavelength of 215 nm.

The sample was applied to the Brownlee analytical column and eluted using a gradient from 0-35% solvent B in 2 min, 35% solvent B in 2 min followed by 35-80% solvent B in 40 min at a flow rate of 1.0 ml/min. Fractions collected were assayed for antibacterial activity. Fractions were tested with the Gram-positive bacteria Streptococcus mutans Ingbritt, Streptococcus sanguinis (formerly S. sanguis), Streptococcus sobrinus 6715 WT15, Staphylococcus aureus ATCC 25923 and the Gram-negative bacteria, Escherichia coli NCTC 10418, Salmonella typhimurium ATCC 13311, and Pseudomonas aeruginosa ATCC 25619. The bacteria were stored in 30% glycerol broths at −20° C.

The antibacterial assay was conducted in sterile 96 well plates (Becton Dickinson, Melbourne, Australia). The growth media for the Gram-positive bacteria consisted of Todd Hewitt broth (TH; 36.4 g/l), Yeast extract (YE; 5 g/l) and 100 mM potassium phosphate, pH 6.28 (TYPB). The media for Gram-negative bacteria consisted of Nutrient broth at pH 6.28 and for P. gingivalis, Brain Heart Infusion media (with 1 µg/ml haeme and 0.5 g/l cysteine) at pH 7.0. An inoculum was prepared by diluting exponentially growing cells in growth media, such that the inoculum contained approximately $2.7 \times 10^4$ viable cells/ml. To each well was added 250 µl media containing the peptide in varying concentrations and 50 µl of bacterial inoculum. Control assays contained all components except peptide. The negative control wells each contained 250 µl media, 50 µl inoculum and 5 µl of gramicidin D (2.5 mM). Growth of the bacterium was determined as the difference between the final and initial Optical Density (OD) 650 nm readings using a microplate reader (BIORAD, model 450, NSW, Australia). The final OD represented the maximum culture OD and was recorded normally 20-30 h after inoculation, during which time the cells were incubated at 37° C. in aerobic conditions except for *P. gingivalis* which was incubated in anaerobic conditions at the same temperature. The minimal inhibitory concentration (MIC) was determined as the lowest concentration of peptide required to inhibit the growth of the bacterium. The peptide concentration varied between 0.05 µM-500 µM The antimicrobial activity of the neutralised starting material (TCA-soluble UF whey) is shown in Table 2.

TABLE 2

Growth inhibition of Gram-positive and Gram-negative bacteria by TCA-soluble UF-whey. Microbial growth was determined by optical density at a wavelength of 650 nm after 30 h incubation at 37° C.

| | Growth Inhibition by TCA-soluble UF-whey % | |
|---|---|---|
| Species | 3.7 mg/ml | 1.9 mg/ml |
| Gram-positive bacteria | | |
| S. mutans | 89 ± 6[a] | 42 ± 11 |
| S. aureus | 47 ± 18 | 18 ± 18 |
| S. sanguinis | NI[b] | NI |
| Gram-negative bacteria | | |
| E. coli | 14 ± 8 | 12 ± 15 |
| S. typhimurium | 8 ± 7 | NI |
| P. aeruginosa | 9 ± 6 | NI |

[a]% mean inhibition of growth ± standard deviation (n = 3-6)
[b]no inhibition

FIG. 4 shows the RP-HPLC of the TCA-soluble UF whey. Five peaks were collected and analysed for antibacterial activity. Peak 4 exhibited the highest specific antimicrobial activity as shown in Table 3. Peak 4 (RP4) was further subjected to gel filtration chromatography using a gel filtration column (Supelco 30×7.8 cm) and eluted using 30% acetonitrile v/v 0.1% TFA in water at a flow rate of 1 ml/min.

TABLE 3

Growth inhibition of streptococcal species by RP-HPLC peaks of UF-whey. The peaks generated were tested in the antibacterial assay. Microbial growth was determined by optical density at a wavelength of 650 nm after 30 h incubation at 37° C.

| | | Assay | % Growth Inhibition | | |
|---|---|---|---|---|---|
| Sample | Amount[†] (mg) | concentration[∞] (mg/ml) | S. mutans | S. sobrinus | S. sanguinis |
| RP1 + RP2 | 1.7 | 1.4 | 23 ± 16[a] | —[b] | NI[c] |
| RP3 | 1.0 | 0.90 | 17 ± 16 | 23 ± 20 | 17 ± 7 |
| RP4 | 0.64 | 0.53 | 91 ± 3 | 81 ± 5 | 26 ± 7 |
| RP5 | 0.60 | 0.50 | 79 ± 7 | 79 ± 14 | 23 ± 5 |

[a]% mean inhibition of growth ± standard deviation (n = 3-6)
[b]not determined
[c]no inhibition
[†]Amount of each peak estimated by 215 nm absorbance
[∞]Concentration of peak in antibacterial assay FIG. 5 shows the gel filtration chromatography of peak 4 (RP4) from RP-HPLC of the TCA-soluble UF whey. Four peaks from the chromatography were collected and assayed for antimicrobial activity against *S. mutans* as shown in Table 4.

TABLE 4

The inhibition of growth of *S. mutans* by gel filtration peaks of peak 4 from RP-HPLC of TCA-soluble whey.

| Peak | Amount[†] (mg) | Assay Concentration[∞] (mg/ml) | % Growth inhibition |
|---|---|---|---|
| RP4GF1 | 3.12 | 2.6 | 46 ± 9[a] |
| RP4GF2 | —[b] | — | NI[c] |
| RP4GF3 | 19.2 | 16 | 26 ± 12 |
| RP4GF4 | 2.88 | 2.4 | 41 ± 11 |

[a]% mean inhibition of growth ± standard deviation (n = 3-6)
[b]not determined
[c]no inhibition
[†]Amount of each peak estimated by 215 nm absorbance
[∞]Concentration of peak in antibacterial assay The four peaks were also analysed by amino acid sequence analysis and by mass spectrometry.

Mass spectrometric analysis (MS) of peptides was performed using a Perspective Biosystems (Framingham, Mass., USA) Voyager linear matrix assisted laser desorption/ionisation Time of Flight (MALDI-TOF) mass spectrometer equipped with delayed extraction. Samples were mixed (1:1 v/v) on the sample analysis plate with a 5 mg/ml solution of 2-5, dihydroxybenzoic acid in 50% aqueous acetonitrile, containing 0.25% v/v TFA in water. All spectra were obtained in linear, positive mode with an accelerating voltage of 20 kV, grid voltage of 92% and pulse delay time of 125 ns. Calibration was performed using bovine insulin (MW 5733.54 Da). For sequence analysis peptides were applied to a preconditioned Hewlett-Packard (HP; Blackburn, Vic, Aust.) sequencing column in 1 ml of sample loading solution (2% v/v TFA in water) and then analysed using a HP G1005A Protein sequencer.

TABLE 5

Comparison of the peaks from gel filtration chromatography of peak 4 (RP4) of TCA-soluble UF whey as determined by sequence and mass spectrometric analysis.

| Peak | Measured Mass (Da) | Calculated Mass (Da) | Assignment[†] |
|---|---|---|---|
| RP4GF1 | 6756 | 6755 | Ser(P)$^{149}$κ-casein-B-(106-169) (SEQ ID NO:8) |
| | 6788 | 6787 | Ser(P)$^{149}$κ-casein-A-(106-169) (SEQ ID NO:10) |
| | 6736 | 6835 | Ser(P)$^{127}$, Ser(P)$^{149}$κ-casein-B-(106-169) (SEQ ID NO:9) |
| | 6869 | 6867 | Ser(P)$^{127}$, Ser(P)$^{149}$κ-casein-A-(106-169) (SEQ ID NO:11) |
| RP4GF2 | — | — | β-lactoglobulin, minor traces of α-lactalbumin and κ-casein (106-169) (SEQ ID NO:16) and (SEQ ID NO:17) |
| RP4GF3 | — | — | α-lactalbumin |
| RP4GF4 | 6758 | 6755 | Ser(P)$^{149}$κ-casein-B-(106-169) (SEQ ID NO:8) |
| | 6788 | 6787 | Ser(P)$^{149}$κ-casein-A-(106-169) (SEQ ID NO:10) |
| | 6738 | 6835 | Ser(P)$^{127}$, Ser(P)$^{149}$κ-casein-B-(106-169) (SEQ ID NO:9) |
| | 6869 | 6867 | Ser(P)$^{127}$, Ser(P)$^{149}$κ-casein-A-(106-169) (SEQ ID NO:11) |

[†]Assigned by N-terminal amino acid sequencing

The two gel filtration peaks with the same specific antimicrobial activity RP4 GF1 and RP4 GF4 (Table 4) contained the same peptides, presumably the higher molecular weight fraction RP4 GF1, represented an aggregated state of the phosphopeptides. The active peptides were identified as:

Ser(P)$^{149}$ κ-casein-B-(106-169) (SEQ ID NO:8)
Ser(P)$^{149}$ κ-casein-A-(106-169) (SEQ ID NO:10)
Ser(P)$^{127}$, Ser(P)$^{149}$ κ-casein-B-(106-169) (SEQ ID NO:9)
Ser(P)$^{127}$, Ser(P)$^{149}$ κ-casein-A-(106-169) (SEQ ID NO:11)

The identification of antimicrobial activity with the phosphorylated, non-glycosylated form of κ-casein (106-169) ((SEQ ID NO:16) and (SEQ ID NO:17)) is consistent with the identification of the tryptic casein peptide Ser(P)$^{149}$ κ-casein (117-169) ((SEQ ID NO:12) and (SEQ ID NO:14)) as an antimicrobial peptide in Example 1.

B. Preparation of Antimicrobial Peptides from TCA-Soluble UF Whey Treated with Endopeptidase Glu-C Endopeptidase Glu-C (Sigma Chemical Co, St. Louis, Mo., USA) was added (5.0 μg/ml) to a solution of TCA-soluble UF-whey (1.0 mg/ml), in ammonium acetate (0.05 M, pH 4.0) and incubated at 37° C. for 24 h. The reaction was stopped by lowering the pH to 3.0 by the addition of glacial acetic acid. Enzymatic digestion products were separated by RP-HPLC.

FIG. 6 shows the RP-HPLC of the endo Glu-C digest of TCA-soluble UF whey. Twelve peaks were collected and only peak 12 exhibited antimicrobial activity against *S. mutans* as shown in Table 6. Peak 12 contained three peptides as shown by sequence and mass spectrometric analyses (Table 7). These peaks were further purified by analytical RP-HPLC and only peptide Ser(P)$^{149}$ κ-casein A (138-158) (SEQ ID NO:4) exhibited antimicrobial activity with a 100 μM concentration giving close to 100% growth inhibition of *S. mutans*.

TABLE 6

Antimicrobial activity against *S. mutans* of lyophilised peaks 9-12 from RP-HPLC of an endo Glu-C hydrolysate of TCA-soluble UF-whey.

| Peak | Amount[†] (mg) | Assay Concentration[∞] (mg/ml) | % Growth inhibition |
|---|---|---|---|
| 9 | 0.64 | 0.53 | NI[a] |
| 10 | 0.30 | 0.25 | NI |
| 11 | 0.32 | 0.27 | NI |
| 12 | 0.40 | 0.34 | 84 ± 9[b] |

[a]no inhibition
[b]% mean inhibition of growth ± standard deviation (n = 3)
[†]Amount of each peak estimated by 215 nm absorbance
[∞]Concentration of peak in antibacterial assay

TABLE 7

Composition of peaks 9-12 from RP-HPLC of an endo Glu-C hydrolysate of TCA-soluble UF-whey.

| Peak | Measured Molecular mass (Da)[a] | Calculated Molecular mass (Da) | Assignment |
|---|---|---|---|
| 9 | 3056.5 | 3050.2 | Ser (P)$^{149}$ κ-casein-B-(141-151) (SEQ ID NO:12) |
| | 4080.9 | 4076.2 | κ-casein-A-1 GalNAc, 1 Gal-(106-140) (SEQ ID NO:17) |
| | 4373.7 | 4367.2 | κ-casein-A-1 GalNAc, 1 Gal, 1 NeuAc-(106-140) + methionine sulfoxide (SEQ ID NO:17) |
| | 4750.9 | 4748.0 | κ-casein-A-2 GalNAc, 2 Gal, 1 NeuAc-(106-140) (SEQ ID NO:17) |
| | 5040.8 | 5039.0 | κ-casein-A-2 GalNAc, 2 Gal, 2 NeuAc-(106-140) + methionine sulfoxide (SEQ ID NO:17) |
| 10 | 2438.2 | 2432.4 | κ-casein-A-1 GalNAc-(119-140) (SEQ ID NO:17) |
| | 2481.9 | 2474.0 | Ser (P)$^{149}$ κ-casein-A-1 GalNAc, 1 NeuAc-(141-158) (SEQ ID NO:14) |
| | 3423.8 | 3423.0 | κ-casein-B-(106-137) (SEQ ID NO:16) |
| | 4092.5 | 4092.2 | κ-casein-A-1 GalNAc, 1 Gal-(106-140) + methionine sulfoxide (SEQ ID NO:17) |
| | 4383.7 | 4383.2 | κ-casein-A-1 GalNAc, 1 Gal, 1 NeuAc-(106-140) + methionine sulfoxide (SEQ ID NO:17) |
| 11 | 1890.1 | 1884.1 | κ-casein-A-(152-169) (SEQ ID NO:19) and k-casein-B-(152-169) (SEQ ID NO:18) |
| | 2938.4 | 2931.2 | κ-casein-A-(119-147) (SEQ ID NO:19) |
| | 3427.4 | 3423.8 | κ-casein-B-(106-137) (SEQ ID NO:16) |
| | 4094.2 | 4088.0 | κ-casein-B-1 GalNAc, 1 Gal-(106-140) (SEQ ID NO:16) |
| | 4385.3 | 4379.0 | κ-casein-B-1 GalNAc, 1 Gal, 1 NeuAc-(106-140) (SEQ ID NO:16) |
| 12 | 2285.6 | 2279.3 | Ser (P)$^{149}$ κ-casein-A-(138-158) (SEQ ID NO:14) |
| | 2356.8 | 2348.4 | Ser (P)$^{149}$ κ-casein-B-(148-169) (SEQ ID NO:12) |
| | 2398.3 | 2392.5 | Ser (P)$^{149}$ κ-casein-A-(148-169) (SEQ ID NO:14) |

[a]molecular mass determined by MS

These results showed that only a 20 residue fragment of Ser(P)$^{149}$ κ-casein A (106-169) (SEQ ID NO:10), Ser(P)$^{149}$ κ-casein A (138-158) (SEQ ID NO:4) displayed antimicrobial activity albeit less potent (100 μM MIC) compared with the longer peptide (2.5 μM MIC). The twenty residue fragment of the two major genetic variants A and B are shown:

Ser(P)$^{149}$ κ-casein A (138-158) AVESTVATLEDSPEV-IESPPE, (SEQ ID NO:4), wherein serine at amino acid residue 12 of SEQ ID NO:4 is a phosphoseryl residue Ser(P)$^{149}$ κ-casein B (138-158) AVESTVATLEASPEV-IESPPE, (SEQ ID NO:3), wherein serine at amino acid residue 12 of SEQ ID NO:3 is a phosphoseryl residue.

The twenty residue fragment is amphipathic and has the potential to form an amphipathic helix and therefore a channel in the bacterial membrane. A molecular model of κ-casein (130-158) ((SEQ ID NO:18) and (SEQ ID NO:19)) as a hexamer forming a polar channel with a non-polar exterior that could allow the passage of cations (Na$^+$, K$^+$, H$^+$ etc.) through a bacterial cell membrane thereby dissipating transmembrane electrochemical gradients was constructed. It was interesting to note that the molecular model of the glycosylated form of κ-casein (130-158) ((SEQ ID NO:18) and (SEQ ID NO:19)), which has no antimicrobial activity, has the channel blocked by sugar residues perhaps thereby possibly explaining the lack of activity with the glycosylated peptides.

C. Synthesis of Ser(P)$^{149}$ κ-Casein (138-160)

To confirm antimicrobial activity of Ser(P)$^{149}$ κ-casern (138-158) ((SEQ ID NO:5) and (SEQ ID NO:6)) related peptides were synthesised with and without the phosphorylation and assayed for antimicrobial activity.

A peptide corresponding to Ser(P)$^{149}$ κ-casein A (138-160) (SEQ ID NO:14), containing a phosphoryl group on Ser 149, and κ-casein A (130-158) (SEQ ID NO:19) were synthesised manually by standard solid-phase peptide synthesis protocols for Fmoc chemistry. The peptides were assembled as the carboxyl form using Pac-Peg-PS resin (PerSeptive Biosystems). Subsequent additions of the remaining Fmoc amino acids including Fmoc-Ser(PO(OBzl)OH)—OH were accomplished with HBTU/HOBt activation using 4 equiv of Fmoc-amino acid and 6 equiv of DIPEA. The Fmoc group was removed with a continuous flow of 2% v/v DBU in DMF containing 2% v/v piperidine for 5 mm. Cleavage of the peptide from the resin support was performed using TFA:TIPS:water (95:2.5:2.5) cleavage cocktail for 2.5 h under N$_2$, in darkness. After cleavage the resin was removed by filtration and the filtrate concentrated under a stream of nitrogen. After the peptide products were precipitated in cold ether, they were centrifuged and washed three times. The peptide precipitate was then dissolved in water containing 0.1% v/v TFA and insoluble residue removed by centrifugation.

Purification of synthesised peptides was performed using a Brownlee C18 preparative column. Chromatograms were developed at a flow rate of 4.0 ml/min and peptides were eluted using a gradient of 0-100% solvent B in 43 min. Peptide fractions collected from the column were applied to the Brownlee C18 analytical column and eluted using a gradient of 0-100% solvent B in 40 min.

All collected peptide fractions were lyophilised and subjected to analysis by MS.

Table 8 shows the antimicrobial activity of the two synthetic peptides. These results show that the phosphorylation of Ser$^{149}$ is essential for full antimicrobial activity. The phosphoseryl residue Ser(P)$^{149}$ may be necessary for the formation of an ion channel in the bacterial membrane or maybe necessary for solubility. Further, the higher MIC (100-150 µM) for the Ser(P)$^{149}$ κ-casein A (138-160) (SEQ ID NO:14) compared with the larger peptide Ser(P)$^{149}$ κ-casein A (117-169) (SEQ ID NO:14) (2.5 µM MIC) suggests that the flanking residues of Ser(P)$^{149}$ κ-casein (138-158) ((SEQ ID NO:3) and (SEQ ID NO:4)) may be necessary for solubility and/or interaction with the bacterial cell and formation of the ion channel.

TABLE 8

Inhibition of S. mutans growth by synthetic peptides κ-casein-A-(130-158) (non-phosphorylated) and Ser (P)$^{149}$ κ-casein-A-(138-160).

| Peptide | MIC | % Growth inhibition Concentration of synthetic peptides (mM) | | | | |
|---|---|---|---|---|---|---|
| | | 100 | 75 | 50 | 25 | 10 |
| κ-casein-A-(130-158) (SEQ ID NO:19) | 1.2 mM | 17 ± 13$^a$ | —$^b$ | 14 ± 13 | 11 ± 7 | NI$^c$ |
| Ser (P)$^{149}$ κ-casein-A-(138-160) (SEQ ID NO:14) | 150 µM | — | 69 ± 6 | 52 ± 5 | 17 ± 9 | 6 ± 10 |

$^a$% mean inhibition of growth ± standard deviation (n = 3-6)
$^b$not determined
$^c$no inhibition

EXAMPLE 3

A. Trypsin Hydrolysis

Sodium caseinate was dissolved in 150 mM NH$_4$HCO$_3$ pH 8.0 at 10% (w/v) and hydrolysed using Novo trypsin (2 g/L) at 50° C. for 2 h. Hydrolysis was terminated by the addition of 1N HCl to pH 4.6 and the undigested protein removed by centrifugation. A sample of the hydrolysate was applied to a 7 µm Applied Biosystems C$_8$ column (4.6×220 mm) and eluted (as described in Example 1. Peaks were collected and assayed for antimicrobial activity against Streptococcus sanguinis. Two peptides showed activity, Ser(P)$^{149}$ κ-casein (117-169) ((SEQ ID NO:12) and (SEQ ID NO:14)) and β-casein (184-202) (SEQ ID NO:7).

B. Rennet Hydrolysis

Casein HCl (5 g) was dissolved in 100 ml of 100 mM ammonium bicarbonate pH 8.0. Once the casein had dissolved the pH was lowered to 6.3 with 1 M HCl and 1 mg of rennet (chymosin, Sigma) was added and the mixture incubated for 1 h at 37° C. TCA (11% w/v) was added to the solution or the pH was lowered to 4.5 by the addition of 1 M HCl and the precipitated proteins were removed by centrifugation. The supernatant was collected, neutralised and lyophilised. The dried sample was dissolved in solvent A (0.1% TFA in water) and applied to a Brownlee C18 preparative RFHPLC column. The column was eluted using a gradient of 15% solvent B for 5 mm 15-60% solvent B in 225 mm followed by 60-100% solvent B in 1 mm at a flow rate of 4.0 ml/min. The eluant was monitored at 215 nm. Four peaks were obtained two of which had antimicrobial activity and corresponded to the non-glycosylated, phosphorylated κ-casein (106-169).

The active peptides were identified as:

Ser(P)$^{149}$ κ-casein A (106-169) (SEQ ID NO:10),

Ser(P)$^{127}$, Ser(P)$^{149}$ κ-casern A (106-169) (SEQ ID NO:11)

and
Ser(P)$^{149}$ κ-casein B (106-169) (SEQ ID NO:8)
Ser(P)$^{127}$, Ser(P)$^{149}$ κ-casern B (106-169) (SEQ ID NO:9).

EXAMPLE 4

Proposed Toothpaste Formulations

Formulation 1

| Ingredient | % w/w |
|---|---|
| Dicalcium phosphate dihydrate | 50.0 |
| Glycerol | 20.0 |
| Sodium carboxyraethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Ser(P)$^{149}$ κ-casein(106-169) (SEQ ID NO:8) and/or (SEQ ID NO:10) | 1.0 |
| Water | balance |

Formulation 2

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Ser(P)$^{149}$ κ-casein(106-169) (SEQ ID NO:8) and/or (SEQ ID NO:10) | 2.0 |
| Water | balance |

Formulation 3

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Ser(P)$^{149}$ κ-casein(106-169) (SEQ ID NO:8) and/or (SEQ ID NO:10) | 5.0 |
| Water | balance |

Formulation 4

| Ingredient | % w/w |
|---|---|
| Sorbitol | 10.0 |
| Irish moss | 1.0 |
| Sodium Hydroxide (50%) | 1.0 |
| Gantrez | 19.0 |
| Water (deionised) | 2.69 |
| Sodium monofluorophosphate | 0.76 |
| Sodium saccharin | 0.3 |
| Pyrophosphate | 2.0 |
| Hydrated alumina | 48.0 |
| Flavour oil | 0.95 |
| Ser(P)$^{149}$ κ-casein(106-169) (SEQ ID NO:8) and/or (SEQ ID NO:10) | 1.0 |
| Water | balance |

Formulation 5

| Ingredient | % w/w |
|---|---|
| Sodium polyacrylate | 50.0 |
| Sorbitol | 10.0 |
| Glycerol | 20.0 |
| Sodium saccharin | 0.1 |
| Sodium monofluorophosphate | 0.3 |
| Chlorhexidine gluconate | 0.01 |
| Ethanol | 3.0 |
| Ser(P)$^{149}$ κ-casein(106-169) (SEQ ID NO:8) and/or (SEQ ID NO:10) | 2.0 |
| Linolic acid | 0.05 |
| Water | balance |

EXAMPLE 5

Proposed Mouthwash Formulations

Formulation 1

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Ser(P)$^{149}$ κ-casein(106-169) (SEQ ID NO:8) and/or (SEQ ID NO:10) | 2.0 |
| Water | balance |

Formulation 2

| Ingredient | % w/w |
|---|---|
| Gantrez S-97 | 2.5 |
| Glycerine | 10.0 |
| Flavour oil | 0.4 |
| Sodium monofluorophosphate | 0.05 |
| Chlorhexidine gluconate | 0.01 |

-continued

| Formulation 2 | |
|---|---|
| Ingredient | % w/w |
| Lauroyl diethanolamide | 0.2 |
| Ser(P)$^{149}$ κ-casein(106-169) (SEQ ID NO:8) and/or (SEQ ID NO:10) | 2.0 |
| Water | Balance |

EXAMPLE 6

Proposed Lozenge Formulation

| Ingredient | % w/w |
|---|---|
| Sugar | 75-80 |
| Corn syrup | 1-20 |
| Flavour oil | 1-2 |
| NaF | 0.01-0.05 |
| Ser(P)$^{149}$ κ-casein(106-169) (SEQ ID NO:8) and/or (SEQ ID NO:10) | 3.0 |
| Mg stearate | 1-5 |
| Water | Balance |

EXAMPLE 7

Proposed Gingival Massage Cream Formulation

| Ingredient | % w/w |
|---|---|
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Chlorohexidine gluconate | 0.5 |
| Sucrose monostearate | 0.1 |
| Ser(P)$^{149}$ κ-casein(106-169) (SEQ ID NO:8) and/or (SEQ ID NO:10) | 3.0 |
| Water | balance |

EXAMPLE 8

Proposed Chewing Gum Formulation

| Ingredient | % w/w |
|---|---|
| Gum base | 30.0 |
| Calcium carbonate | 2.0 |
| Crystalline sorbitol | 53.0 |
| Glycerine | 0.5 |
| Flavour oil | 0.1 |

-continued

| Ingredient | % w/w |
|---|---|
| Ser(P)$^{149}$ κ-casein(106-169) (SEQ ID NO:8) and/or (SEQ ID NO:10) | 2.0 |
| Water | Balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Addy M (1988) Rationale for chemotherapy in the treatment of periodontal disease In: *Periodontology Today* Guggenheim B (ed) pp 281-289, Basel: Karger.

Bevins C L, Zasloff M (1990) Peptides from frog skin. *Ann Rev Biochem.* 59: 395-414.

Boman H G, Hultmark D (1987) Cell-free immunity in insects. *Ann Rev Microbiol* 41: 103-126

Brown L J, Oliver R C, Loe H (1989) Periodontal diseases in the US in 1981: Prevalence, severity, extent and role in tooth mortality. *J Periodontol* 60: 363-370.

Casteels P, Ampe C, Jacobs F, Vaeck M, Tempst P (1989) Apidaecins: antibacterial peptides from honeybees. *EMBO J* 8: 2387-2391.

Christersson L A, Zambon J J, Dunford R G, Grossi S G, Genco R J (1989) Specific subgingival bacteria and diagnosis of gingivitis and periodontitis. *J Dent Res* 68: 1633-1639.

Clark D P, Durell S, Maloy W L, Zasloff M (1994) Ranalexin. A novel antimicrobial peptide from bullfrog (*Rana catesbeiana*) skin, structurally related to the bacterial antibiotic, polymyxin. *J Biol Chem* 269: 10849-10855.

Loesch W J (1976) The Gingival Index, the plaque index and the retention index systems *J Periodontol* 38: 610-616.

Marsh P D (1991) Dentifrices containing new agents for the control of plaque and gingivitis: microbiological aspects. *J Clin Periodontol* 18: 462-467.

Migliore-Samour D, Floch F, Jolles P (1989) Biologically active casein peptides implicated in immunomodulation. *J Dairy Res* 56: 357-362.

Moore L V H, Moore W E C, Cato E P, Smibert R M, Burmeister J A, Best A M, Ranney R R (1987) Bacteriology of human gingivitis *J Dent Res* 66: 989-995.

Mor A, Nicolas P (1994) Isolation and structure of novel defensive peptides from frog skin. *Eur J Biochem* 219: 145-154.

Rogers A H, Reynolds E C (1990) The utilisation of casein and amino acids by *Streptococcus sanguis* $P_4A_7$ in continuous culture. *J. Gen. Microbiol.* 136: 2545-2550.

Romeo D, Skerlavaj B, Bolognesi M, Gennaro R (1988) Structure and bactericidal activity of an antibiotic dodecapeptide purified from bovine neutrophils. *J Biol Chem* 263: 9573-9575.

Simmaco M, Barra D, Chiarini F, Noviello L, Melchiorri P, Kreil G, Richter K (1991) A family of bombinin-related peptides from the skin of Bombina variegate. *Eur J Biochem* 199: 217-222.

Spencer A J, Wright F A C, Brown D F, Hammond R H, Lewis J M (1985) A socio-dental study of adult periodontal health: Melbourne, 1985 *Community Dental Health Monograph No* 5, Melbourne University Press.

Svedberg J, de Haas J, Leimenstoll G, Paul F, Teschemacher H (1985) Demonstration of β-casomorphin immunoreactive materials in in vivo digests of bovine milk and in small intestine contents after bovine milk ingestion in adult humans *Peptides* 6: 825-830.

Zanetti M, Storici P, Tossi A, Scocchi M, Gennaro R (1994) Molecular cloning and chemical synthesis of a novel antibacterial peptide derived from pig myeloid cells. *J Biol Chem* 269: 7855-7858.

Zucht H D, Raida M, Adermann K, Magert H J, Forssmann W G (1995) Casocidin-I: a casein-alpha s2 derived peptide exhibits antibacterial activity. *FEBS Lett.* 25, 372(2-3): 185-188.

The invention claimed is:

1. A method of treating or prophylactically treating dental caries or periodontal disease in a subject, the method comprising the step of administering a peptide to the teeth or gums of the subject in need of such treatment, wherein the peptide is selected from:
   a) a peptide consisting of the amino acid sequence AVESTVATLEASPEVIESPPE (SEQ ID NO:3), wherein serine at amino acid residue 12 of SEQ ID NO:3 is a phosphoseryl residue;
   b) a peptide consisting of the amino acid sequence AVESTVATLEDSPEVIESPPE (SEQ ID NO:4), wherein serine at amino acid residue 12 of SEQ ID NO:4 is a phosphoseryl residue;
   c) MAIPPKKNQDKTEIPTINTIASGEPTSTPTIEAVESTVATLEASPEV-IESPPEINTVQVTSTAV (SEQ ID NO:8), wherein serine at amino acid residue 44 of SEQ ID NO:8 is a phosphoseryl residue;
   d) a peptide consisting of the amino acid sequence MAIPPKKNQDKTEIPTINTIASGEPTSTP-TIEAVESTVATLEASPEVIESPPEINTVQVTSTAV (SEQ ID NO:9), wherein serine at amino acid residue 22 and amino acid residue 44 of SEQ ID NO:9 are phosphoseryl residues;
   e) MAIPPKKNQDKTEIPTINTIASGEPTSTPTTEAVESTVATLEDSPEV-IESPPEINTVQVTSTAV (SEQ ID NO:10), wherein serine at amino acid residue 44 of SEQ ID NO:10 is a phosphoseryl residue;
   f) MAIPPKKNQDKTEIPTINTIASGEPTSTPTTEAVESTVATLEDSPEV-IESPPEINTVQVTSTAV (SEQ ID NO: 11), wherein serine at amino acid residue 22 and amino acid residue 44 of SEQ ID NO:11 are phosphoseryl residues;
   g) a peptide consisting of the amino acid sequence TEIPTINTIASGEPTSTPTIEAVEST-VATLEASPEVIESPPEINTVQVTSTAV (SEQ ID NO:12), wherein serine at amino acid residue 33 of SEQ ID NO:12 is a phosphoseryl residue;
   h) a peptide consisting of the amino acid sequence TEIPTINTIASGEPTSTPTIEAVEST-VATLEASPEVIESPPEINTVQVTSTAV (SEQ ID NO:13), wherein serine at amino acid residue 11 and serine at amino acid residue 33 of SEQ ID NO:13 are phosphoseryl residues;
   i) a peptide consisting of the amino acid sequence TEIPTINTIASGEPTSTPTTEAVEST-VATLEDSPEVIESPPEINTVQVTSTAV (SEQ ID NO:14), wherein serine at amino acid residue 33 of SEQ ID NO:14 is a phosphoseryl residue; and
   j) a peptide consisting of the amino acid sequence TEIPTINTIASGEPTSTPTTEAVEST-VATLEDSPEVIESPPEINTVQVTSTAV (SEQ ID NO:15), wherein serine at amino acid residue 11 and serine at amino acid residue 33 of SEQ ID NO:15 are phosphoseryl residues.

2. The method of claim 1, wherein the peptide is administered with a pharmaceutically acceptable carrier.

3. The method of claim 1, wherein the peptide is administered in a composition comprising sodium monofluorophosphate, chlorhexidine gluconate, or both sodium monofluorophosphate and chlorhexidine gluconate.

4. A method of treating or prophylactically treating dental caries or periodontal disease in a subject, the method comprising the step of administering to the teeth or gums of the subject non-glycosylated, antimicrobial peptide comprising less than about 100 amino acids and comprising an amino acid sequence selected from:
   AVESTVATLEASPEVIESPPE (SEQ ID NO:3), wherein serine at amino acid residue 12 of SEQ ID NO:3 is a phosphoseryl residue; and
   AVESTVATLEDSPEVIESPPE (SEQ ID NO:4), wherein serine at amino acid residue 12 of SEQ ID NO:4 is a phosphoseryl residue.

5. The method of claim 4, wherein the peptide comprises less than about 70 amino acids.

6. The method of claim 4, wherein the peptide is administered with a pharmaceutically acceptable carrier.

7. The method of claim 4, wherein the peptide is administered in a composition comprising sodium monofluorophosphate, chlorhexidine gluconate, or both sodium monofluorophosphate and chlorhexidine gluconate.

8. A composition comprising:
   a) a peptide selected from:
      i) a peptide consisting of the amino acid sequence AVESTVATLEASPEVIESPPE (SEQ ID NO:3), wherein serine at amino acid residue 12 of SEQ ID NO:3 is a phosphoseryl residue;
      ii) a peptide consisting of the amino acid sequence AVESTVATLEDSPEVIESPPE (SEQ ID NO:4), wherein serine at amino acid residue 12 of SEQ ID NO:4 is a phosphoseryl residue;
      iii) a peptide consisting of the amino acid sequence TEIPTINTIASGEPTSTPTIEAVEST-VATLEASPEVIESPPEINTVQVTSTAV (SEQ ID NO:12), wherein serine at amino acid residue 33 of SEQ ID NO:12 is a phosphoseryl residue;
      iv) a peptide consisting of the amino acid sequence TEIPTINTIASGEPTSTPTIEAVEST-VATLEASPEVIESPPEINTVQVTSTAV (SEQ ID NO:13), wherein serine at amino acid residue 11 and serine at amino acid residue 33 of SEQ ID NO:13 are phosphoseryl residues;
      v) a peptide consisting of the amino acid sequence TEIPTINTIASGEPTSTPTTEAVEST-VATLEDSPEVIESPPEINTVQVTSTAV (SEQ ID NO:14), wherein serine at amino acid residue 33 of SEQ ID NO:14 is a phosphoseryl residue; and vi) a peptide consisting of the amino acid sequence TEIPTINTIASGEPTSTPTTEAVESTVATLEDSPEVIESPPEINTVQVTSTAV (SEQ ID NO:15), wherein serine at amino acid residue 11 and serine at amino acid residue 33 of SEQ ID NO:15 are phosphoseryl residues; and b) a pharmaceutically acceptable carrier.

9. The composition of claim 8, wherein the pharmaceutically acceptable carrier comprises sodium monofluorophosphate.

10. The composition of claim 8, wherein the pharmaceutically acceptable carrier comprises chlorhexidine gluconate.

11. A non-glycosylated, antimicrobial peptide conjugated to an acyl group, and wherein the peptide is selected from:

a) a peptide consisting of the amino acid sequence AVESTVATLEASPEVIESPPE (SEQ ID NO:3), wherein serine at amino acid residue 12 of SEQ ID NO:3 is a phosphoseryl residue;

b) a peptide consisting of the amino acid sequence AVESTVATLEDSPEVIESPPE (SEQ ID NO:4), wherein serine at amino acid residue 12 of SEQ ID NO:4 is a phosphoseryl residue;

c) a peptide consisting of the amino acid sequence MAIPPKKNQDKTEIPTINTIASGEPTSTPTIEAVESTVATLEASPEVIESPPEINTVQVTSTAV (SEQ ID NO:8), wherein serine at amino acid residue 44 of SEQ ID NO:8 is a phosphoseryl residue;

d) a peptide consisting of the amino acid sequence MAIPPKKNQDKTEIPTINTIASGEPTSTPTIEAVESTVATLEASPEVIESPPEINTVQVTSTAV (SEQ ID NO:9), wherein serine at amino acid residue 22 and amino acid residue 44 of SEQ ID NO:9 are phosphoseryl residues;

e) a peptide consisting of the amino acid sequence MAIPPKKNQDKTEIPTINTIASGEPTSTPTTEAVESTVATLEDSPEVIESPPEINTVQVTSTAV (SEQ ID NO:10), wherein serine at amino acid residue 44 of SEQ ID NO:10 is a phosphoseryl residue;

f) a peptide consisting of the amino acid sequence MAIPPKKNQDKTEIPTINTIASGEPTSTPTTEAVESTVATLEDSPEVIESPPEINTVQVTSTAV (SEQ ID NO: 11), wherein serine at amino acid residue 22 and amino acid residue 44 of SEQ ID NO:11 are phosphoseryl residues;

g) a peptide consisting of the amino acid sequence TEIPTINTIASGEPTSTPTIEAVESTVATLEASPEVIESPPEINTVQVTSTAV (SEQ ID NO:12), wherein serine at amino acid residue 33 of SEQ ID NO:12 is a phosphoseryl residue;

h) a peptide consisting of the amino acid sequence TEIPTINTIASGEPTSTPTIEAVESTVATLEASPEVIESPPEINTVQVTSTAV (SEQ ID NO:13), wherein serine at amino acid residue 11 and serine at amino acid residue 33 of SEQ ID NO:13 are phosphoseryl residues;

i) a peptide consisting of the amino acid sequence TEIPTINTIASGEPTSTPTTEAVESTVATLEDSPEVIESPPEINTVQVTSTAV (SEQ ID NO:14), wherein serine at amino acid residue 33 of SEQ ID NO:14 is a phosphoseryl residue; and j) a peptide consisting of the amino acid sequence TEIPTINTIASGEPTSTPTTEAVESTVATLEDSPEVIESPPEINTVQVTSTAV (SEQ ID NO:15), wherein serine at amino acid residue 11 and serine at amino acid residue 33 of SEQ ID NO:15 are phosphoseryl residues.

12. A peptide of claim 11, wherein the acyl group is a fatty acid.

13. A composition comprising:
a) a peptide according to claim 11; and
b) a pharmaceutically acceptable carrier.

14. The composition of claim 13, wherein the pharmaceutically acceptable carrier comprises sodium monofluorophosphate.

15. A method of treating or prophylactically treating dental caries or periodontal disease in a subject, the method comprising the step of administering the composition of claim 14 to the teeth or gums of the subject in need of such treatment.

16. The composition of claim 13, wherein the pharmaceutically acceptable carrier comprises chlorhexidine gluconate.

17. A method of treating or prophylactically treating dental caries or periodontal disease in a subject, the method comprising the step of administering the composition of claim 16 to the teeth or gums of the subject in need of such treatment.

18. A method of treating or prophylactically treating dental caries or periodontal disease in a subject, the method comprising the step of administering a peptide as claimed in claim 11 to the teeth or gums of the subject in need of such treatment.

19. A non-glycosylated, antimicrobial peptide consisting of the amino acid sequence AVESTVATLEASPEVIESPPE (SEQ ID NO:3), wherein serine at amino acid residue 12 of SEQ ID NO:3 is a phosphoseryl residue.

20. A non-glycosylated, antimicrobial peptide consisting of the amino acid sequence AVESTVATLEDSPEVIESPPE (SEQ ID NO:4), wherein serine at amino acid residue 12 of SEQ ID NO:4 is a phosphoseryl residue.

21. A non-glycosylated, antimicrobial peptide consisting of the amino acid sequence MAIPPKKNQDKTEIPTINTIASGEPTSTPTIEAVESTVATLEASPEVIESPPEINTVQVTSTAV (SEQ ID NO:9), wherein serine at amino acid residue 22 and amino acid residue 44 of SEQ ID NO:9 are phosphoseryl residues.

22. A non-glycosylated, antimicrobial peptide consisting of the amino acid sequence TEIPTINTIASGEPTSTPTIEAVESTVATLEASPEVIESPPEINTVQVTSTAV (SEQ ID NO:12), wherein serine at amino acid residue 33 of SEQ ID NO:12 is a phosphoseryl residue.

23. A non-glycosylated, antimicrobial peptide consisting of the amino acid sequence TEIPTINTIASGEPTSTPTIEAVESTVATLEASPEVIESPPEINTVQVTSTAV (SEQ ID NO:13), wherein serine at amino acid residue 11 and serine at amino acid residue 33 of SEQ ID NO:13 are phosphoseryl residues.

24. A non-glycosylated, antimicrobial peptide consisting of the amino acid sequence TEIPTINTIASGEPTSTPTTEAVESTVATLEDSPEVIESPPEINTVQVTSTAV (SEQ ID NO:14), wherein serine at amino acid residue 33 of SEQ ID NO:14 is a phosphoseryl residue.

25. A non-glycosylated, antimicrobial peptide consisting of the amino acid sequence TEIPTINTIASGEPTSTPTTEAVESTVATLEDSPEVIESPPEINTVQVTSTAV (SEQ ID NO:15), wherein serine at amino acid residue 11 and serine at amino acid residue 33 of SEQ ID NO:15 are phosphoseryl residues.

* * * * *

```
                         SEQUENCE LISTING

<160> NUMBER OF SEQ ID NOS: 19

<210> SEQ ID NO 1
<211> LENGTH: 6
<212> TYPE: PRT
<213> ORGANISM: bovine

<400> SEQUENCE: 1

Pro Gly Pro Ile Pro Asn
1               5

<210> SEQ ID NO 2
<211> LENGTH: 6
<212> TYPE: PRT
<213> ORGANISM: bovine

<400> SEQUENCE: 2

Thr Thr Met Pro Leu Trp
1               5

<210> SEQ ID NO 3
<211> LENGTH: 21
<212> TYPE: PRT
<213> ORGANISM: Bovine
<220> FEATURE:
<221> NAME/KEY: PHOSPHORYLATION
<222> LOCATION: (12)...(12)
<223> OTHER INFORMATION: phosphoseryl residue

<400> SEQUENCE: 3

Ala Val Glu Ser Thr Val Ala Thr Leu Glu Ala Ser Pro Glu Val Ile
1               5                   10                  15

Glu Ser Pro Pro Glu
            20

<210> SEQ ID NO 4
<211> LENGTH: 21
<212> TYPE: PRT
<213> ORGANISM: bovine
<220> FEATURE:
<221> NAME/KEY: PHOSPHORYLATION
<222> LOCATION: (12)...(12)
<223> OTHER INFORMATION: phosphoseryl residue

<400> SEQUENCE: 4

Ala Val Glu Ser Thr Val Ala Thr Leu Glu Asp Ser Pro Glu Val Ile
1               5                   10                  15

Glu Ser Pro Pro Glu
            20

<210> SEQ ID NO 5
<211> LENGTH: 21
<212> TYPE: PRT
<213> ORGANISM: bovine
```

```
<400> SEQUENCE: 5

Ala Val Glu Ser Thr Val Ala Thr Leu Glu Ala Ser Pro Glu Val Ile
 1               5                  10                  15

Glu Ser Pro Pro Glu
            20

<210> SEQ ID NO 6
<211> LENGTH: 21
<212> TYPE: PRT
<213> ORGANISM: bovine

<400> SEQUENCE: 6

Ala Val Glu Ser Thr Val Ala Thr Leu Glu Asp Ser Pro Glu Val Ile
 1               5                  10                  15

Glu Ser Pro Pro Glu
            20

<210> SEQ ID NO 7
<211> LENGTH: 19
<212> TYPE: PRT
<213> ORGANISM: bovine

<400> SEQUENCE: 7

Asp Met Pro Ile Gln Ala Phe Leu Leu Tyr Gln Gln Pro Val Leu Gly
 1               5                  10                  15

Pro Val Arg

<210> SEQ ID NO 8
<211> LENGTH: 64
<212> TYPE: PRT
<213> ORGANISM: bovine
<220> FEATURE:
<221> NAME/KEY: PHOSPHORYLATION
<222> LOCATION: (44)...(44)
<223> OTHER INFORMATION: phosphoseryl residue

<400> SEQUENCE: 8

Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Ile Glu
            20                  25                  30

Ala Val Glu Ser Thr Val Ala Thr Leu Glu Ala Ser Pro Glu Val Ile
        35                  40                  45

Glu Ser Pro Pro Glu Ile Asn Thr Val Gln Val Thr Ser Thr Ala Val
    50                  55                  60

<210> SEQ ID NO 9
<211> LENGTH: 64
<212> TYPE: PRT
<213> ORGANISM: bovine
<220> FEATURE:
<221> NAME/KEY: PHOSPHORYLATION
<222> LOCATION: (22)...(22)
<223> OTHER INFORMATION: phosphoseryl residue
<220> FEATURE:
<221> NAME/KEY: PHOSPHORYLATION
<222> LOCATION: (44)...(44)
<223> OTHER INFORMATION: phosphoseryl residue

<400> SEQUENCE: 9

Met Ala Ile Pro Pro Lys Lys Asn Gln Asp Lys Thr Glu Ile Pro Thr
 1               5                  10                  15
```

```
Ile Asn Thr Ile Ala Ser Gly Glu Pro Thr Ser Thr Pro Thr Ile Glu
            20                  25                  30

Ala Val Glu Ser Thr Val Ala Thr Leu Glu Ala Ser Pro Glu Val Ile
            35                  40                  45

Glu Ser Pro Pro Glu Ile Asn Thr Val Gln Val Thr Ser Thr Ala Val
 50                  55                  60
```

```
<210> SEQ ID NO 10
<211> LENGTH: 64
<212> TYPE: PRT
<213> ORGANISM: bovine
<220> FEATURE:
<221> NAME/KEY: PHOSPHORYLATION
<222> LOCATION: (44)...(44)
<223> OTHER INFORMATION: phosphoseryl residue

<400> SEQUENCE: 10
```

```
Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Thr Glu
            20                  25                  30

Ala Val Glu Ser Thr Val Ala Thr Leu Glu Asp Ser Pro Glu Val Ile
            35                  40                  45

Glu Ser Pro Pro Glu Ile Asn Thr Val Gln Val Thr Ser Thr Ala Val
 50                  55                  60
```

```
<210> SEQ ID NO 11
<211> LENGTH: 64
<212> TYPE: PRT
<213> ORGANISM: bovine
<220> FEATURE:
<221> NAME/KEY: PHOSPHORYLATION
<222> LOCATION: (22)...(22)
<223> OTHER INFORMATION: phosphoseryl residue
<220> FEATURE:
<221> NAME/KEY: PHOSPHORYLATION
<222> LOCATION: (44)...(44)
<223> OTHER INFORMATION: phosphoseryl residue

<400> SEQUENCE: 11
```

```
Met Ala Ile Pro Pro Lys Lys Asn Gln Asp Lys Thr Glu Ile Pro Thr
 1               5                  10                  15

Ile Asn Thr Ile Ala Ser Gly Glu Pro Thr Ser Thr Pro Thr Thr Glu
            20                  25                  30

Ala Val Glu Ser Thr Val Ala Thr Leu Glu Asp Ser Pro Glu Val Ile
            35                  40                  45

Glu Ser Pro Pro Glu Ile Asn Thr Val Gln Val Thr Ser Thr Ala Val
 50                  55                  60
```

```
<210> SEQ ID NO 12
<211> LENGTH: 53
<212> TYPE: PRT
<213> ORGANISM: bovine
<220> FEATURE:
<221> NAME/KEY: PHOSPHORYLATION
<222> LOCATION: (33)...(33)
<223> OTHER INFORMATION: phosphoseryl residue

<400> SEQUENCE: 12
```

```
Thr Glu Ile Pro Thr Ile Asn Thr Ile Ala Ser Gly Glu Pro Thr Ser
 1               5                  10                  15

Thr Pro Thr Ile Glu Ala Val Glu Ser Thr Val Ala Thr Leu Glu Ala
            20                  25                  30
```

Ser Pro Glu Val Ile Glu Ser Pro Glu Ile Asn Thr Val Gln Val
        35                  40                  45

Thr Ser Thr Ala Val
    50

<210> SEQ ID NO 13
<211> LENGTH: 53
<212> TYPE: PRT
<213> ORGANISM: bovine
<220> FEATURE:
<221> NAME/KEY: PHOSPHORYLATION
<222> LOCATION: (11)...(11)
<223> OTHER INFORMATION: phosphoseryl residue
<220> FEATURE:
<221> NAME/KEY: PHOSPHORYLATION
<222> LOCATION: (33)...(33)
<223> OTHER INFORMATION: phosphoseryl residue

<400> SEQUENCE: 13

Thr Glu Ile Pro Thr Ile Asn Thr Ile Ala Ser Gly Glu Pro Thr Ser
  1               5                  10                  15

Thr Pro Thr Ile Glu Ala Val Glu Ser Thr Val Ala Thr Leu Glu Ala
            20                  25                  30

Ser Pro Glu Val Ile Glu Ser Pro Glu Ile Asn Thr Val Gln Val
        35                  40                  45

Thr Ser Thr Ala Val
    50

<210> SEQ ID NO 14
<211> LENGTH: 53
<212> TYPE: PRT
<213> ORGANISM: bovine
<220> FEATURE:
<221> NAME/KEY: PHOSPHORYLATION
<222> LOCATION: (33)...(33)
<223> OTHER INFORMATION: phosphoseryl residue

<400> SEQUENCE: 14

Thr Glu Ile Pro Thr Ile Asn Thr Ile Ala Ser Gly Glu Pro Thr Ser
  1               5                  10                  15

Thr Pro Thr Thr Glu Ala Val Glu Ser Thr Val Ala Thr Leu Glu Asp
            20                  25                  30

Ser Pro Glu Val Ile Glu Ser Pro Glu Ile Asn Thr Val Gln Val
        35                  40                  45

Thr Ser Thr Ala Val
    50

<210> SEQ ID NO 15
<211> LENGTH: 53
<212> TYPE: PRT
<213> ORGANISM: bovine
<220> FEATURE:
<221> NAME/KEY: PHOSPHORYLATION
<222> LOCATION: (11)...(11)
<223> OTHER INFORMATION: phosphoseryl residue
<220> FEATURE:
<221> NAME/KEY: PHOSPHORYLATION
<222> LOCATION: (33)...(33)
<223> OTHER INFORMATION: phosphoseryl residue

<400> SEQUENCE: 15

Thr Glu Ile Pro Thr Ile Asn Thr Ile Ala Ser Gly Glu Pro Thr Ser
  1               5                  10                  15

Thr Pro Thr Thr Glu Ala Val Glu Ser Thr Val Ala Thr Leu Glu Asp
            20                  25                  30

```
Ser Pro Glu Val Ile Glu Ser Pro Glu Ile Asn Thr Val Gln Val
        35                  40                  45
Thr Ser Thr Ala Val
        50
```

<210> SEQ ID NO 16
<211> LENGTH: 64
<212> TYPE: PRT
<213> ORGANISM: bovine

<400> SEQUENCE: 16

```
Met Ala Ile Pro Pro Lys Lys Asn Gln Asp Lys Thr Glu Ile Pro Thr
1               5                   10                  15

Ile Asn Thr Ile Ala Ser Gly Glu Pro Thr Ser Thr Pro Thr Ile Glu
            20                  25                  30

Ala Val Glu Ser Thr Val Ala Thr Leu Glu Ala Ser Pro Glu Val Ile
        35                  40                  45

Glu Ser Pro Pro Glu Ile Asn Thr Val Gln Val Thr Ser Thr Ala Val
    50                  55                  60
```

<210> SEQ ID NO 17
<211> LENGTH: 64
<212> TYPE: PRT
<213> ORGANISM: bovine

<400> SEQUENCE: 17

```
Met Ala Ile Pro Pro Lys Lys Asn Gln Asp Lys Thr Glu Ile Pro Thr
1               5                   10                  15

Ile Asn Thr Ile Ala Ser Gly Glu Pro Thr Ser Thr Pro Thr Thr Glu
            20                  25                  30

Ala Val Glu Ser Thr Val Ala Thr Leu Glu Asp Ser Pro Glu Val Ile
        35                  40                  45

Glu Ser Pro Pro Glu Ile Asn Thr Val Gln Val Thr Ser Thr Ala Val
    50                  55                  60
```

<210> SEQ ID NO 18
<211> LENGTH: 53
<212> TYPE: PRT
<213> ORGANISM: bovine

<400> SEQUENCE: 18

```
Thr Glu Ile Pro Thr Ile Asn Thr Ile Ala Ser Gly Glu Pro Thr Ser
1               5                   10                  15

Thr Pro Thr Ile Glu Ala Val Glu Ser Thr Val Ala Thr Leu Glu Ala
            20                  25                  30

Ser Pro Glu Val Ile Glu Ser Pro Glu Ile Asn Thr Val Gln Val
        35                  40                  45

Thr Ser Thr Ala Val
        50
```

<210> SEQ ID NO 19
<211> LENGTH: 53
<212> TYPE: PRT
<213> ORGANISM: bovine

<400> SEQUENCE: 19

```
Thr Glu Ile Pro Thr Ile Asn Thr Ile Ala Ser Gly Glu Pro Thr Ser
1               5                   10                  15

Thr Pro Thr Thr Glu Ala Val Glu Ser Thr Val Ala Thr Leu Glu Asp
```

-continued

```
                20              25              30
Ser Pro Glu Val Ile Glu Ser Pro Pro Glu Ile Asn Thr Val Gln Val
        35                      40                      45

Thr Ser Thr Ala Val
    50
```